(12) United States Patent
Yamaguchi

(10) Patent No.: US 9,528,141 B2
(45) Date of Patent: Dec. 27, 2016

(54) NUCLEAR LOCALIZATION OF SRC-FAMILY TYROSINE KINASES IS REQUIRED FOR GROWTH FACTOR-INDUCED EUCHROMATINIZATION

(71) Applicant: National University Corporation Chiba University, Chiba (JP)

(72) Inventor: Naoto Yamaguchi, Chiba (JP)

(73) Assignee: National University Corporation Chiba University, Chiba (JP)

( * ) Notice: Subject to any disclaimer, the term of this patent is extended or adjusted under 35 U.S.C. 154(b) by 0 days.

(21) Appl. No.: 13/998,823

(22) Filed: Dec. 11, 2013

(65) Prior Publication Data

US 2014/0120527 A1 May 1, 2014

Related U.S. Application Data

(62) Division of application No. 12/658,966, filed on Feb. 18, 2010, now Pat. No. 8,663,947.

(60) Provisional application No. 61/153,681, filed on Feb. 19, 2009.

(51) Int. Cl.

| | | |
|---|---|---|
| C12Q 1/68 | (2006.01) | |
| G01N 1/30 | (2006.01) | |
| G01N 21/64 | (2006.01) | |
| G01N 21/17 | (2006.01) | |
| G01N 21/00 | (2006.01) | |

(52) U.S. Cl.
CPC .............. *C12Q 1/68* (2013.01); *G01N 21/6428* (2013.01); *G01N 21/00* (2013.01); *G01N 2021/1765* (2013.01)

(58) Field of Classification Search
CPC ...... C12Q 1/68; G01N 21/00; G01N 21/6428; G01N 2021/1765
USPC ................................................ 435/6.1, 40.5
See application file for complete search history.

(56) References Cited

U.S. PATENT DOCUMENTS

| | | | |
|---|---|---|---|
| 6,022,961 | A | 2/2000 | Yamamoto et al. |
| 2004/0127468 | A1 | 7/2004 | Tatton |
| 2004/0171091 | A1 | 9/2004 | Lesko et al. |
| 2006/0154234 | A1 | 7/2006 | Winther et al. |

FOREIGN PATENT DOCUMENTS

| | | | |
|---|---|---|---|
| WO | 9743732 | A1 | 11/1997 |
| WO | 0062247 | A1 | 10/2000 |

OTHER PUBLICATIONS

Cowden et al., "Microfluorometric Investigations of Chromatin Structure," Histochemistry, vol. 72, 1981, pp. 11-23.

Diaz et al., "Nuclear pattern recognition by two-parameter texture analysis," Computer Methods and Programs in Biomedicine, vol. 49, 1996, pp. 1-9.

Aoyama et al., "Nuclear c-Abl-mediated tyrosine phosphorylation induces chromatin structural changes through histone modifications that include H4K16 hypoacetylation", Experimental Cell Research, vol. 317, 2011, pp. 2874-2903.

Best et al., "Apoptosis: Basic Concepts and Implications in Coronary Artery Disease", Journal of the American Heart Association, Arterioscler Thromb Vasc Biol., vol. 19, 1999, pp. 14-22.

Bodega et al., "Repetitive elements dynamics in cell identity programming, maintenance and disease", Current Opinion in Cell Biology, vol. 31, 2014, pp. 67-73.

Bright et al., "Apoptosis: Programmed Cell Death in Health and Disease", Bioscience Reports, vol. 14, No. 2, 1994, pp. 67-81.

Coppede, "The potential of epigenetic therapies in neurodegenerative diseases", Frontiers in Genetics, vol. 5, Art. 220, Jul. 2014, pp. 1-8.

Elmore, "Apoptosis: A Review of Programmed Cell Death", Toxicol Pathol., vol. 35(4), 2007, pp. 495-516.

Ghavami et al., "Autophagy and apoptosis dysfunction in neurodegenerative disorders", Progress in Neurobiology, vol. 112, 2014, pp. 24-49.

Klein et al., "Epigenetic regulation: Basic concepts and relevance to neurologic disease", Neurology, vol. 82, No. 20, May 20, 2014 (abstract only).

Liyanage et al., "DNA Modifications: Function and Applications in Normal and Disease States", Biology, vol. 3, 2014, pp. 670-723.

Nijhawan et al., "Apoptosis in Neural Development and Disease", Annu. Rev. Neurosci., vol. 23, 2000, pp. 73-87.

Peters, "The role of genomic imprinting in biology and disease: an expanding view", Nature Reviews: Genetics, vol. 15, Aug. 2014, pp. 517-530.

Reshi et al., "RNA Viruses: ROS-Mediated Cell Death", International Journal of Cell Biology, vol. 2014, Art. 467452, May 8, 2014, pp. 1-17.

Silva et al., "Diagnosis and classification of autoimmune orchitis", Autoimmunity Reviews, vol. 13, 2014, pp. 431-434.

Venderova et al., "Programmed Cell Death in Parkinson's Disease", Cold Spring Harb Perspect in Med, vol. 2: a009365, 2012, pp. 1-23.

Widlak et al., "Roles of the Major Apoptotic Nuclease—DNA Fragmentation Factor—in Biology and Disease", Cell. Mol. Life Sci., vol. 66, 2009, pp. 263-274.

Ban et al., "BCR-ABL1 mediates up-regulation of Fyn in chronic myelogenous leukemia," Blood Journal, 2008, vol. 111, No. 5, pp. 2904-2908.

Dehm et al., "SRC gene expression in human cancer: the role of transcriptional activation," Biochemistry and Cell Biology, 2004, vol. 82, No. 2, pp. 263-274.

(Continued)

*Primary Examiner* — Shin Lin Chen

(74) *Attorney, Agent, or Firm* — Kilyk & Bowersox, P.L.L.C.

(57) ABSTRACT

A method for quantitatively evaluating chromatin structural changes using pixel imaging of the nucleus is provided. Pixel imaging of the nucleus can include capturing one or more images of a nucleus of one or more nucleic acid stain treated cells. The stain intensity can be measured by quantitating the intensity. The mean and/or standard deviation of stain intensity per pixel can be used to determine chromatin condensation levels or chromatin structural change.

8 Claims, 49 Drawing Sheets
(30 of 49 Drawing Sheet(s) Filed in Color)

(56) References Cited

OTHER PUBLICATIONS

Klaunig et al., "The Role of Oxidative Stress in Carcinogenesis," Annual Review of Pharmacology and Toxicology, 2004, vol. 44, pp. 239-267.
Klaunig et al., "Oxidative Stress and Oxidative Damage in Carcinogenesis," Toxicologic Pathology, 2010, vol. 38, pp. 96-109.
Kubota et al., "Role for tyrosine phosphorylation of A-kinase anchoring protein 8 (AKAP8) in its dissociation from chromatin and the nuclear matrix," The Journal of Biological Chemistry, Mar. 13, 2015, (24 pages).
Reuter et al., "Oxidative Stress, inflammation, and cancer: How are they linked?," Free Radical Biology & Medicine, 2010, vol. 49, No. 11, pp. 1603-1616 (40 pages).
Zink et al., "Nuclear Structure in Cancer Cells," Nature Reviews Cancer, vol. 4, 2004, pp. 677-687.
Fischer et al., "Ras-Associated Nuclear Structural Change Appears Functionally Significant and Independent of the Mitotic Signaling Pathway," Journal of Cellular Biochemistry, vol. 70, 1998, pp. 130-140.
Komitowski et al., "Quantitative Features of Chromatin Structure in the Prognosis of Breast Cancer," Cancer, vol. 65, 1990, pp. 2725-2730.

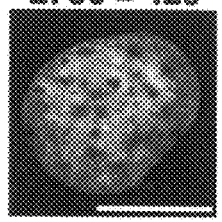
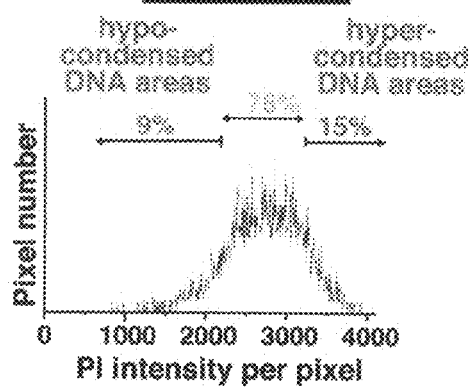
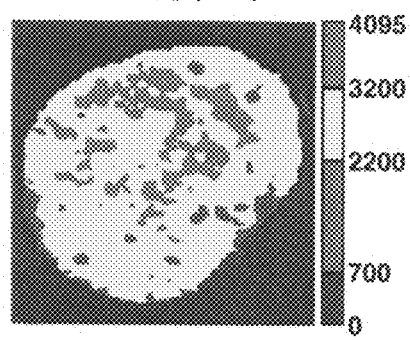
Fig. 1A
Fig. 1B
Fig. 1C

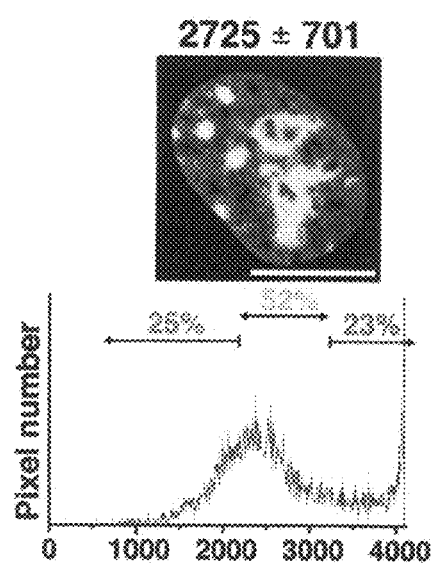
Fig. 4A
Fig. 4B
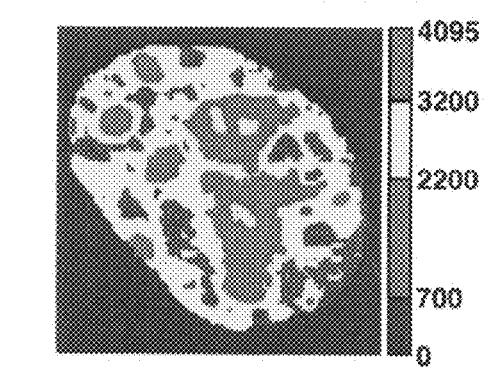
Fig. 4C

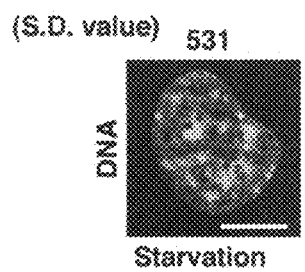
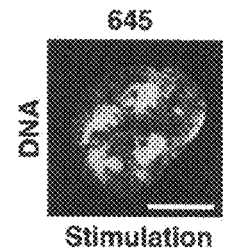
Fig. 14A  Fig. 14B
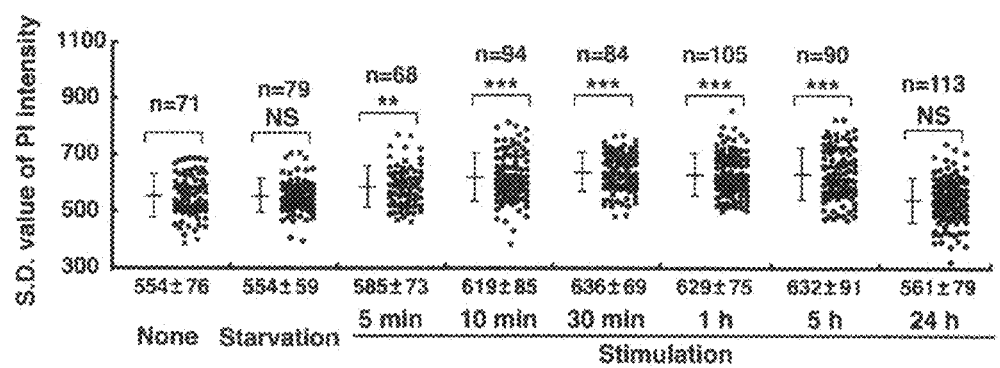
Fig. 15

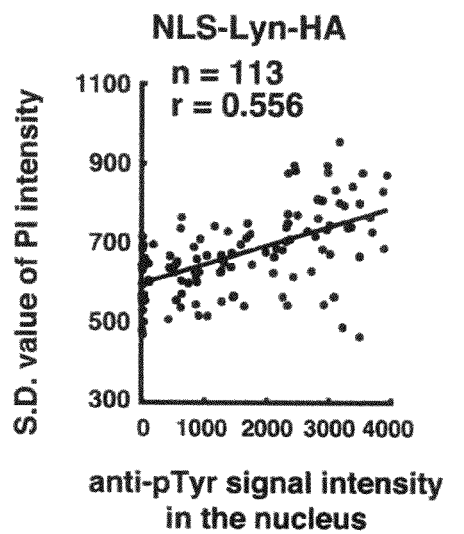
Fig. 41
Fig. 42
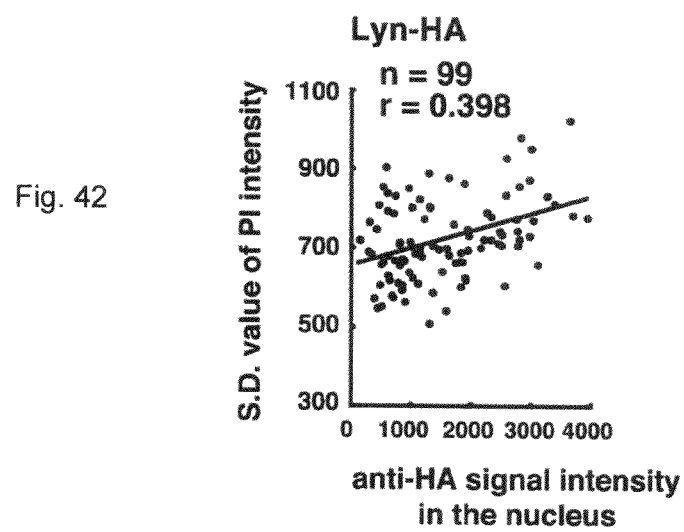

SEQUENCE LISTING

<160> NUMBER OF SEQ ID NOS: 1

<210> SEQ ID NO 1
<211> LENGTH: 25
<212> TYPE: PRT
<213> ORGANISM: Artificial Sequence
<220> FEATURE:
<223> OTHER INFORMATION: Plasmid

<400> SEQUENCE: 1

Ile Pro Glu Phe Pro Arg Asp Pro Leu Cys Trp Thr Arg Pro Ala Ala
1               5                   10                  15

Pro Lys Leu Ser Pro Arg Ala Gly Asn
            20                  25

NUCLEAR LOCALIZATION OF SRC-FAMILY TYROSINE KINASES IS REQUIRED FOR GROWTH FACTOR-INDUCED EUCHROMATINIZATION

This application is a divisional of U.S. patent application Ser. No. 12/658,966, filed Feb. 18, 2010, which claims the benefit under 35 U.S.C. §119(e) of prior U.S. Provisional Patent Application No. 61/153,681, filed Feb. 19, 2009, which is incorporated in its entirety by reference herein.

FIELD

The present invention relates to the use of pixel imaging as a tool for quantitative analysis of chromatin structural changes.

Src-family tyrosine kinases (SFKs), which form the largest subfamily of nonreceptor-type protein-tyrosine kinases, consist of proto-oncogene products and structurally related proteins and include at least eight highly homologous proteins: c-Src, Lyn, Fyn, c-Yes, c-Fgr, Hck, Lck, and Blk [1, 2]. c-Src, Lyn, Fyn, and c-Yes are widely expressed in various cell types, whereas c-Fgr, Hck, Lck, and Blk are found primarily in hematopoietic cells [2]. The tyrosine kinase activity of SFKs is tightly regulated by tyrosine phosphorylation and dephosphorylation, and SFKs play a pivotal role in cell proliferation, differentiation, migration, and cytoskeletal reorganization [1, 2]. SFKs are mainly located at the cytoplasmic face of the plasma membrane but are found at late endosomes/lysosomes, secretory granules/phagosomes, and the Golgi apparatus [1-9].

Tyrosine kinases and phosphatases are well known to function as signaling molecules downstream of extracellular stimuli at the plasma membrane. However, several tyrosine kinases and phosphatases reside in the nucleus and may regulate tyrosine phosphorylation and dephosphorylation of nuclear proteins [10-12]. Src-family kinases (SFKs), which participate in various signaling events, are found at not only the plasma membrane but also several subcellular compartments, including the nucleus. Emerging evidence show that some of SFKs localize to the nucleus and function as signaling molecules in DNA damage response, apoptosis and cell cycle regulation [13-19], suggesting the importance of SFKs in nuclear events associated with nuclear tyrosine phosphorylation. Nuclear structural changes are frequently observed during transcription, cell differentiation, senescence, tumorigenesis, and cell cycle. The role of signal transduction in the alteration of chromatin texture, however, has not been extensively explored in the past.

Chromatin is the state in which DNA is packaged with histones in the nucleus. Chromatin is generally composed of transcriptionally permissive, less-condensed euchromatin and highly condensed and often repressed heterochromatin [20]. Chromatin organization in interphase influences gene expression, DNA replication, damage, and repair. Chromatin structure dynamically changes and associates with epigenetic gene regulation. Alterations of nuclear architecture, including chromatin structural changes, can be characteristic of a given tumor type and stage, which are often used in cancer diagnosis [21]. Recent evidence suggests that phosphorylation is involved in chromatin structural changes. Phosphorylation of the serine 10 residue of histone H3 (histone H3S10) is crucial for chromatin condensation during mitosis and meiosis [22, 23].

However, the role of nuclear tyrosine phosphorylation in chromatin architecture has not been previously elucidated.

The references below and all publications mentioned herein are incorporated in their entirety by reference herein.

[1] M. T. Brown, J. A. Cooper, Regulation, substrates and functions of src, Biochim. Biophys. Acta 1287 (1996) 121-149.

[2] S. M. Thomas, J. S. Brugge, Cellular functions regulated by Src family kinases, Annu. Rev. Cell Dev. Biol. 13 (1997) 513-609.

[3] K. B. Kaplan, J. R. Swedlow, H. E. Varmus, D. O. Morgan, Association of $p60^{c-src}$ with endosomal membranes in mammalian fibroblasts, J. Cell Biol. 118 (1992) 321-333.

[4] H. Möhn, V. Le Cabec, S. Fischer, I. Maridonneau-Parini, The src-family protein-tyrosine kinase $p59^{hck}$ is located on the secretory granules in human neutrophils and translocates towards the phagosome during cell activation, Biochem. J. 309 (1995) 657-665.

[5] K. Kasahara, Y. Nakayama, K. Ikeda, Y. Fukushima, D. Matsuda, S. Horimoto, N. Yamaguchi, Trafficking of Lyn through the Golgi caveolin involves the charged residues on αE and αI helices in the kinase domain, J. Cell Biol. 165 (2004) 641-652.

[6] D. Matsuda, Y. Nakayama, S. Horimoto, T. Kuga, K. Ikeda, K. Kasahara, N. Yamaguchi, Involvement of Golgi-associated Lyn tyrosine kinase in the translocation of annexin II to the endoplasmic reticulum under oxidative stress, Exp. Cell Res. 312 (2006) 1205-1217.

[7] K. Kasahara, Y. Nakayama, A. Kihara, D. Matsuda, K. Ikeda, T. Kuga, Y. Fukumoto, Y. Igarashi, N. Yamaguchi, Rapid trafficking of c-Src, a non-palmitoylated Src-family kinase, between the plasma membrane and late endosomes/lysosomes, Exp. Cell Res. 313 (2007) 2651-2666.

[8] K. Kasahara, Y. Nakayama, I. Sato, K. Ikeda, M. Hoshino, T. Endo, N. Yamaguchi, Role of Src-family kinases in formation and trafficking of macropinosomes, J. Cell. Physiol. 211 (2007) 220-232.

[9] K. Kasahara, Y. Nakayama, N. Yamaguchi, v-Src and c-Src, nonpalmitoylated Src-family kinases, induce perinuclear accumulation of lysosomes through Rab7 in a kinase activity-independent manner, Cancer Lett. 262 (2008) 19-27.

[10] C. Cans, R. Mangano, D. Barilá, G. Neubauer, G. Superti-Furga, Nuclear tyrosine phosphorylation: the beginning of a map, Biochem. Pharmacol. 60 (2000) 1203-1215.

[11] M. Bollen, M. Beullens, Signaling by protein phosphatases in the nucleus, Trends Cell Biol. 12 (2002) 138-145.

[12] G. B. Moorhead, L. Trinkle-Mulcahy, A. Ulke-Lemée, Emerging roles of nuclear protein phosphatases, Nat. Rev. Mol. Cell Biol. 8 (2007) 234-244.

[13] S. Kharbanda, A. Saleem, Z. M. Yuan, S. Kraeft, R. Weichselbaum, L. B. Chen, D. Kufe, Nuclear signaling induced by ionizing radiation involves colocalization of the activated $p56/p53^{lyn}$ tyrosine kinase with $p34^{cdc2}$, Cancer Res. 56 (1996) 3617-3621.

[14] Z. M. Yuan, Y. Huang, S. K. Kraeft, L. B. Chen, S. Kharbanda, D. Kufe, Interaction of cyclin-dependent kinase 2 and the Lyn tyrosine kinase in cells treated with 1-beta-D-arabinofuranosylcytosine, Oncogene 13 (1996) 939-946.

[15] K. Yoshida, R. Weichselbaum, S. Kharbanda, D. Kufe, Role for Lyn tyrosine kinase as a regulator of stress-activated protein kinase activity in response to DNA damage, Mol. Cell. Biol. 20 (2000) 5370-5380.

[16] N. Yamaguchi, Y. Nakayama, T. Urakami, S. Suzuki, T. Nakamura, T. Suda, N. Oku, Overexpression of the Csk

[17] K. Ikeda, Y. Nakayama, Y. Togashi, Y. Obata, T. Kuga, K. Kasahara, Y. Fukumoto, N. Yamaguchi, Nuclear localization of Lyn tyrosine kinase mediated by inhibition of its kinase activity, Exp. Cell Res. 314 (2008) 3392-3404.

[18] I. Chu, J. Sun, A. Arnaout, H. Kahn, W. Hanna, S. Narod, P. Sun, C. K. Tan, L. Hengst, J. Slingerland, p27 phosphorylation by Src regulates inhibition of cyclin E-Cdk2, Cell 128 (2007) 281-294.

[19] M. Grimmler, Y. Wang, T. Mund, Z. Cilensek, E. M. Keidel, M. B. Waddell, H. Jäkel, M. Kullmann, R. W. Kriwacki, L. Hengst, Cdk-inhibitory activity and stability of p27Kip1 are directly regulated by oncogenic tyrosine kinases, Cell 128 (2007) 269-280.

[20] A. I. Lamond, W. C. Earnshaw, Structure and function in the nucleus, Science 280 (1998) 547-553.

[21] D. Zink, A. H. Fischer, J. A. Nickerson, Nuclear structure in cancer cells, Nat. Rev. Cancer 4 (2004) 677-687.

[22] C. Prigent, S. Dimitrov, Phosphorylation of serine 10 in histone H3, what for?, J. Cell Sci. 116 (2003) 3677-3685.

[23] S. J. Nowak, V. G. Corces, Phosphorylation of histone H3: a balancing act between chromosome condensation and transcriptional activation, Trends Genet. 20 (2004) 214-220.

[24] J. D. Bjorge, C. Bellagamba, H. C. Cheng, A. Tanaka, J. H. Wang, D. J. Fujita, Characterization of two activated mutants of human pp60$^{c-src}$ that escape c-Src kinase regulation by distinct mechanisms, J. Biol. Chem. 270 (1995) 24222-24228.

[25] Y. Yamanashi, S. Fukushige, K. Semba, J. Sukegawa, N. Miyajima, K. Matsubara, T. Yamamoto, K. Toyoshima, The yes-related cellular gene lyn encodes a possible tyrosine kinase similar to p56$^{lck}$, Mol. Cell. Biol. 7 (1987) 237-243.

[26] T. Tezuka, H. Umemori, T. Akiyama, S. Nakanishi, T. Yamamoto, PSD-95 promotes Fyn-mediated tyrosine phosphorylation of the N-methyl-D-aspartate receptor subunit NR2A, Proc. Natl. Acad. Sci. USA 96 (1999) 435-440.

[27] J. Sukegawa, K. Semba, Y. Yamanashi, M. Nishizawa, N. Miyajima, T. Yamamoto, K. Toyoshima, Characterization of cDNA clones for the human c-yes gene, Mol. Cell. Biol. 7 (1987) 41-47.

[28] C. L. Law, S. P. Sidorenko, K. A. Chandran, K. E. Draves, A. C. Chan, A. Weiss, S. Edelhoff, C. M. Disteche, E. A. Clark, Molecular cloning of human Syk. A B cell protein-tyrosine kinase associated with the surface immunoglobulin M-B cell receptor complex, J. Biol. Chem. 269 (1994) 12310-12319.

[29] S. Hubner, C. Y. Xiao, D. A. Jans, The protein kinase CK2 site (Ser111/112) enhances recognition of the simian virus 40 large T-antigen nuclear localization sequence by importin, J. Biol. Chem. 272 (1997) 17191-17195.

[30] Y. Nakayama, N. Yamaguchi, Multi-lobulation of the nucleus in prolonged S phase by nuclear expression of Chk tyrosine kinase, Exp. Cell Res. 304 (2005) 570-581.

[31] Y. Nakayama, A. Kawana, A. Igarashi, N. Yamaguchi, Involvement of the N-terminal unique domain of Chk tyrosine kinase in Chk-induced tyrosine phosphorylation in the nucleus, Exp. Cell Res. 312 (2006) 2252-2263.

[32] N. Fujita, S. Watanabe, T. Ichimura, S. Tsuruzoe, Y. Shinkai, M. Tachibana, T. Chiba, M. Nakao, Methyl-CpG binding domain 1 (MBD1) interacts with the Suv39h1- HP1 heterochromatic complex for DNA methylation-based transcriptional repression, J. Biol. Chem. 278 (2003) 24132-24138.

[33] Y. Nakatani, V. Ogryzko, Immunoaffinity purification of mammalian protein complexes. Methods Enzymol. 370 (2003) 430-444.

[34] T. Tamura, T. Kunimatsu, S. T. Yee, O. Igarashi, M. Utsuyama, S. Tanaka, S. Miyazaki, K. Hirokawa, H. Nariuchi, Molecular mechanism of the impairment in activation signal transduction in CD4$^+$ T cells from old mice, Int. Immunol. 12 (2000) 1205-1215.

[35] N. Yamaguchi, M. N. Fukuda, Golgi retention mechanism of β-1,4-galactosyltransferase: membrane-spanning domain-dependent homodimerization and association with α- and β-tubulins, J. Biol. Chem. 270 (1995) 12170-12176.

[36] M. Shimizu, H. Nakamura, T. Hirabayashi, A. Suganami, Y. Tamura, T. Murayama, Ser515 phosphorylation-independent regulation of cytosolic phospholipase A2α (cPLA2α) by calmodulin-dependent protein kinase: possible interaction with catalytic domain A of cPLA2α, Cell. Signal. 20 (2008) 815-824.

[37] R. A. Klinghoffer, C. Sachsenmaier, J. A. Cooper, P. Soriano, Src family kinases are required for integrin but not PDGFR signal transduction, EMBO J. 18 (1999) 2459-2471.

[38] Y. Durocher, S. Perret, A. Kamen, High-level and high-throughput recombinant protein production by transient transfection of suspension-growing human 293-EBNA1 cells, Nucleic Acids Res. 30 (2002) E9.

[39] M. Izumi, H. Miyazawa, T. Kamakura, I. Yamaguchi, T. Endo, F. Hanaoka, Blasticidin S-resistance gene (bsr): a novel selectable marker for mammalian cells, Exp. Cell Res. 197 (1991) 229-233.

[40] T. Kanda, K. F. Sullivan, G. M. Wahl, Histone-GFP fusion protein enables sensitive analysis of chromosome dynamics in living mammalian cells, Curr. Biol. 8 (1998) 377-385.

[41] Y. W. Lam, C. E. Lyon, A. I. Lamond, Large-scale isolation of Cajal bodies from HeLa cells, Mol. Biol. Cell 13 (2002) 2461-2473.

[42] K. Kasahara, Y. Nakayama, Y. Nakazato, K. Ikeda, T. Kuga, N. Yamaguchi, Src signaling regulates completion of abscission in cytokinesis through ERK/MAPK activation at the midbody, J. Biol. Chem. 282 (2007) 5327-5339.

[43] T. Kuga, M. Hoshino, Y. Nakayama, K. Kasahara, K. Ikeda, Y. Obata, A. Takahashi, Y. Higashiyama, Y. Fukumoto, N. Yamaguchi, Role of Src-family kinases in formation of the cortical actin cap at the dorsal cell surface, Exp. Cell Res. 314 (2008) 2040-2054.

[44] J. Tada, M. Omine, T. Suda, N. Yamaguchi, A common signaling pathway via Syk and Lyn tyrosine kinases generated from capping of the sialomucins CD34 and CD43 in immature hematopoietic cells, Blood 93 (1999) 3723-3735.

[45] E. Minc, Y. Allory, H. J. Worman, J. C. Courvalin, B. Buendia, Localization and phosphorylation of HP1 proteins during the cell cycle in mammalian cells, Chromosoma 108 (1999) 220-234.

[46] A. Hirao, I. Hamaguchi, T. Suda, N. Yamaguchi, Translocation of the Csk homologous kinase (Chk/Hyl) controls activity of CD36-anchored Lyn tyrosine kinase in thrombin-stimulated platelets, EMBO J. 16 (1997) 2342-2351.

[47] J. P. Mitchell, N. S. Cohn, M. Van der Ploeg, Quantitative changes in the degree of chromatin condensation during the cell cycle in differentiating Pisum sativum vascular tissue, Histochemistry 78 (1983) 101-109.

[48] H. Santos-Rosa, R. Schneider, A. J. Bannister, J. Sherriff, B. E. Bernstein, N. C. Emre, S. L. Schreiber, J. Mellor, T. Kouzarides, Active genes are tri-methylated at K4 of histone H3, Nature 419 (2002) 407-411.

[49] S. Gupta, D. Campbell, B. Derijard, R. J. Davis, Transcription factor ATF2 regulation by the JNK signal transduction pathway, Science 267 (1995) 389-393.

[50] C. Livingstone, G. Patel, N. Jones, ATF-2 contains a phosphorylation-dependent transcriptional activation domain, EMBO J. 14 (1995) 1785-1797.

[51] I. Hers, C. J. Bell, A. W. Poole, D. Jiang, R. M. Denton, E. Schaefer, J. M. Tavaré, Reciprocal feedback regulation of insulin receptor and insulin receptor substrate tyrosine phosphorylation by phosphoinositide 3-kinase in primary adipocytes, Biochem. J. 368 (2002) 875-884.

[52] G. Huyer, S. Liu, J. Kelly, J. Moffat, P. Payette, B. Kennedy, G. Tsaprailis, M. J. Gresser, C. Ramachandran, Mechanism of inhibition of protein-tyrosine phosphatases by vanadate and pervanadate, J. Biol. Chem. 272 (1997) 843-851.

[53] A. K. Jain, A. K. Jaiswal, GSK-3β acts upstream of Fyn kinase in regulation of nuclear export and degradation of NF-E2 related factor 2, J. Biol. Chem. 282 (2007) 16502-16510.

[54] R. Schmitz, G. Baumann, H. Gram, Catalytic specificity of phosphotyrosine kinases Blk, Lyn, c-Src and Syk as assessed by phage display, J. Mol. Biol. 260 (1996) 664-677.

[55] M. Tachibana, K. Sugimoto, M. Nozaki, J. Ueda, T. Ohta, M. Ohki, M. Fukuda, N. Takeda, H. Niida, H. Kato, Y. Shinkai, G9a histone methyltransferase plays a dominant role in euchromatic histone H3 lysine 9 methylation and is essential for early embryogenesis, Genes Dev. 16 (2002) 1779-1791.

[56] R. H. Tao, I. N. Maruyama, All EGF(ErbB) receptors have preformed homo- and heterodimeric structures in living cells. J. Cell Sci. 121 (2008) 3207-3217.

[57] T. Kuga, Y. Nakayama, M. Hoshino, Y. Higashiyama, Y. Obata, D. Matsuda, K. Kasahara, Y. Fukumoto, N. Yamaguchi, Differential mitotic activation of endogenous c-Src, c-Yes, and Lyn in HeLa cells, Arch. Biochem. Biophys. 466 (2007) 116-124.

[58] T. Cremer, M. Cremer, S. Dietzel, S. Müller, I. Solovei, S. Fakan, Chromosome territories—a functional nuclear landscape, Curr. Opin. Cell Biol. 18 (2006) 307-316.

[59] E. Meshorer, T. Misteli, Chromatin in pluripotent embryonic stem cells and differentiation, Nat. Rev. Mol. Cell Biol. 7 (2006) 540-546.

[60] P. Blume-Jensen, T. Hunter, Oncogenic kinase signaling, Nature 411 (2001) 355-365.

[61] D. Plehn-Dujowich, P. Bell, A. M. Ishov, C. Baumann, G. G. Maul, Non-apoptotic chromosome condensation induced by stress: delineation of interchromosomal spaces, Chromosoma 109 (2000) 266-279.

[62] Y. Shav-Tal, X. Darzacq, S. M. Shenoy, D. Fusco, S. M. Janicki, D. L. Spector, R. H. Singer, Dynamics of single mRNPs in nuclei of living cells, Science 304 (2004) 1797-1800.

[63] H. Albiez, M. Cremer, C. Tiberi, L. Vecchio, L. Schermelleh, S. Dittrich, K. Küpper, B. Joffe, T. Thormeyer, J. von Hase, S. Yang, K. Rohr, H. Leonhardt, I. Solovei, C. Cremer, S. Fakan, T. Cremer, Chromatin domains and the interchromatin compartment form structurally defined and functionally interacting nuclear networks, Chromosome Res. 14 (2006) 707-733.

[64] G. Manning, D. B. Whyte, R. Martinez, T. Hunter, S. Sudarsanam, The protein kinase complement of the human genome, Science 298 (2002) 1912-1934.

[65] S. H. Ahn, W. L. Cheung, J. Y. Hsu, R. L. Diaz, M. M. Smith, C. D. Allis, Sterile 20 kinase phosphorylates histone H2B at serine 10 during hydrogen peroxide-induced apoptosis in S. cerevisiae, Cell 120 (2005) 25-36.

[66] W. Fischle, B. S. Tseng, H. L. Dormann, B. M. Ueberheide, B. A. Garcia, J. Shabanowitz, D. F. Hunt, H. Funabiki, C. D. Allis, Regulation of HP1-chromatin binding by histone H3 methylation and phosphorylation, Nature 438 (2005) 1116-1122.

[67] T. Kouzarides, Chromatin modifications and their function, Cell 128 (2007) 693-705.

[68] M. Dundr, T. Misteli, Functional architecture in the cell nucleus, Biochem. J. 356 (2001) 297-310.

[69] D. K. Pokholok, J. Zeitlinger, N. M. Hannett, D. B. Reynolds, R. A. Young, Activated signal transduction kinases frequently occupy target genes, Science 313 (2006) 533-536.

[70] M. A. Meyn III, S. J. Schreiner, T. P. Dumitrescu, G. J. Nau, T. E. Smithgall, SRC family kinase activity is required for murine embryonic stem cell growth and differentiation, Mol. Pharmacol. 68 (2005) 1320-1330.

[71] A. H. Fischer, D. N. Chadee, J. A. Wright, T. S. Gansler, J. R. Davie, Ras-associated nuclear structural change appears functionally significant and independent of the mitotic signaling pathway, J. Cell. Biochem. 70 (1998) 130-140.

[72] D. Komitowski, C. Janson, Quantitative features of chromatin structure in the prognosis of breast cancer, Cancer 65 (1990) 2725-2730.

SUMMARY

A feature of the present invention is to quantitatively evaluate chromatin structural changes in one or more cells using a pixel imaging method. The method for evaluating chromatin structure in one or more cells can comprise providing a sample of one or more cells and treating the one or more cells with a nucleic acid stain. An image of a nucleus, comprising a plurality of pixels, of one or more of the nucleic acid stain treated cells can be captured. The stain intensity at each pixel of the plurality of pixels can be quantitated and the mean and standard deviation (SD) values of stain intensity per pixel can be calculated. Levels of chromatin condensation can be quantitated based on the SD value of stain intensity per pixel. Chromatin structural changes can be determined based on the levels of chromatin condensation.

Another feature of the present invention is to provide a method for diagnosis, prognosis, or monitoring of a lesion in a subject using the method for evaluating chromatin structure. Chromatin structure can be evaluated for a sample of lesion cells from the subject. A disease state can be determined based on the SD value of stain intensity per pixel.

Another feature of the present invention is to provide a method for diagnosis, prognosis, or monitoring of cancer in a subject using the method for evaluating chromatin structure. Chromatin structure can be evaluated for a sample of cancerous cells from the subject. A malignant disease can be determined based on the SD value of stain intensity per pixel.

Another feature of the present invention is to provide a method of screening for a compound that modulates the chromatin structure of a cell using the method for evaluating chromatin structure. A sample of cells can be contacted with the compound and the chromatin structure in the sample of cells can be evaluated. The SD value of stain intensity per pixel of the cells contacted with the compound can be compared to the SD value of stain intensity per pixel of control cells to identify a compound that modulates the chromatin structure of a cell.

Another feature of the present invention is to provide a system for evaluating the chromatin structure in a cell. The system can comprise an optical device for capturing at least one image of a nucleus of one or more nucleic acid stain treated cells and a spectrometer device for quantitating the stain intensity at each pixel of the image. The spectrometer device can be optically connected to the optical device and operably connected to a calculating device. The system can further include a calculating device for calculating the mean and standard deviation (SD) values of stain intensity per pixel and a display device for displaying the calculated mean and SD values.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows DNA fluorescence images obtained with propidium iodide (PI) staining.

FIG. 1B shows a histogram representing areas of hypocondensed, moderately condensed, and hypercondensed DNA.

FIG. 1C shows a 2D isometric intensity profile corresponding to the image of FIG. 1A.

FIG. 4A shows DNA fluorescence images obtained with propidium iodide (PI) staining.

FIG. 4B shows a histogram representing areas of hypocondensed, moderately condensed, and hypercondensed DNA.

FIG. 4C shows a 2D isometric intensity profile corresponding to the image of FIG. 4A.

FIGS. 14A and 14B show fluorescence images of DNA staining for COS-1 cells that were starved for 24 h under low serum conditions (0.05% FBS) and stimulated with serum (5% FBS) for 5 h, respectively.

FIG. 15 shows a plot representing each S.D. value of PI intensity per pixel for each cell, and bars and values represent means±S.D. from a representative experiment.

FIG. 41 shows 2D-plot analyses shown with S.D. value of PI intensity (vertical axis) versus mean fluorescence intensity of anti-pTyr staining in the nucleus (horizontal axis).

FIG. 42 shows 2D-plot analyses shown with S.D. value of PI intensity (vertical axis) versus mean fluorescence intensity of anti-HA staining in the nucleus (horizontal axis).

DETAILED DESCRIPTION

Figure 2A:
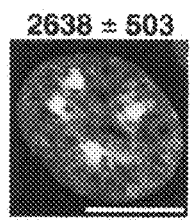
FIG. 2A shows DNA fluorescence images obtained with propidium iodide (PI) staining.
Figure 2B:
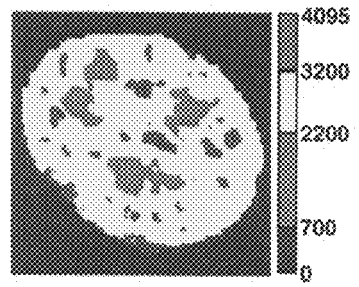
FIG. 2B shows a histogram representing areas of hypocondensed, moderately condensed, and hypercondensed DNA.
Figure 2C:
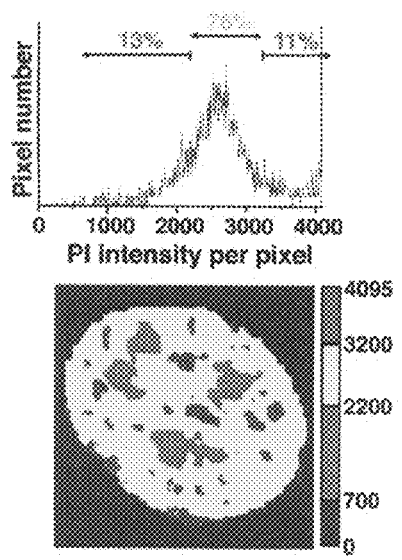
FIG. 2C shows a 2D isometric intensity profile corresponding to the image of FIG. 2A.
Figure 3A:
FIG. 3A shows DNA fluorescence images obtained with propidium iodide (PI) staining.
Figure 3B:
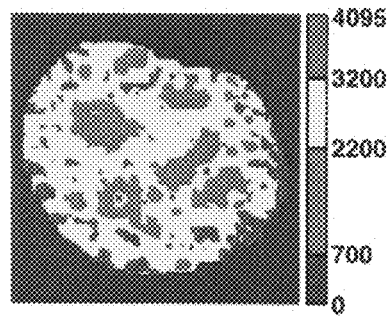
FIG. 3B shows a histogram representing areas of hypocondensed, moderately condensed, and hypercondensed DNA.
Figure 3C:
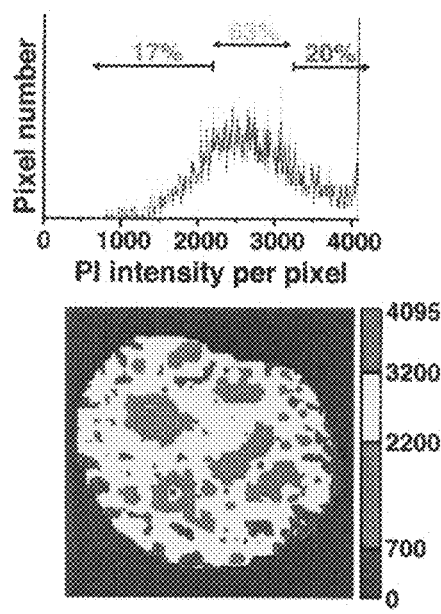
FIG. 3C shows a 2D isometric intensity profile corresponding to the image of FIG. 3A.
Figure 5A:
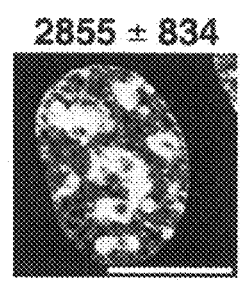
FIG. 5A shows DNA fluorescence images obtained with propidium iodide (PI) staining.
Figure 5B:
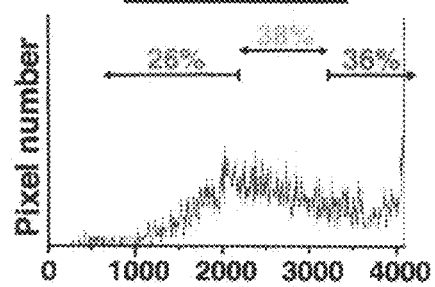
FIG. 5B shows a histogram representing areas of hypocondensed, moderately condensed, and hypercondensed DNA.
Figure 5C:
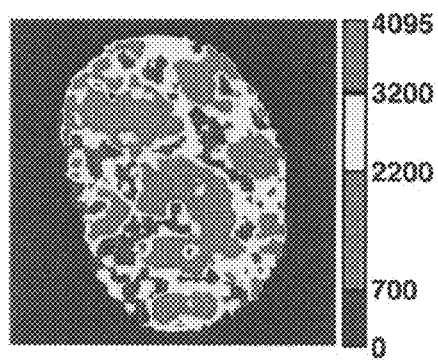
FIG. 5C shows a 2D isometric intensity profile corresponding to the image of FIG. 5A.
Figure 6A:
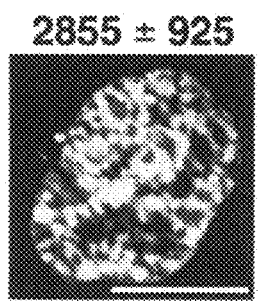
FIG. 6A shows DNA fluorescence images obtained with propidium iodide (PI) staining.
Figure 6B:
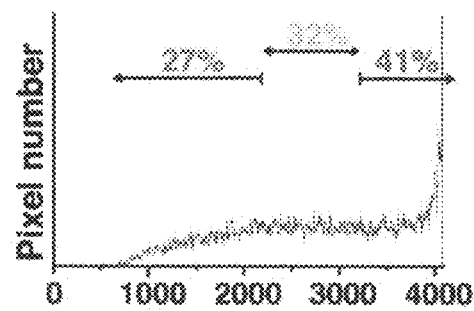
FIG. 6B shows a histogram representing areas of hypocondensed, moderately condensed, and hypercondensed DNA.
Figure 6C:
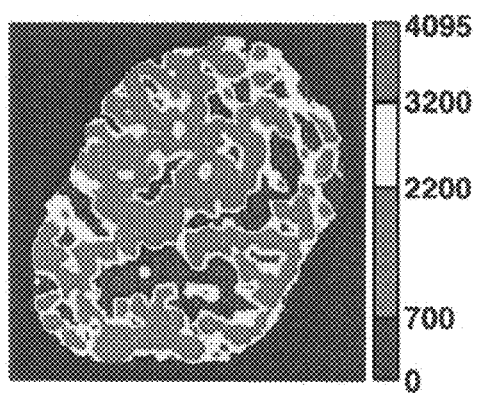
FIG. 6C shows a 2D isometric intensity profile corresponding to the image of FIG. 6A.

The present invention relate to a method for quantitatively evaluating chromatin structural changes using pixel imaging of the nucleus. Pixel imaging of the nucleus can comprise capturing one or more images of a nucleus of one or more nucleic acid stain treated cells. The stain intensity can be measured by quantitating the intensity. The mean and/or standard deviation of stain intensity per pixel can be used to determine chromatin condensation levels or chromatin structural change.

The present inventors have also found that the role of SFKs in chromatin architecture can be determined by determining chromatin condensation levels. According to the present teachings, growth factor stimulation can increase levels of euchromatic hypocondensation and concomitant heterochromatic hypercondensation through nuclear tyrosine phosphorylation mediated by SFKs.

Upon growth factor stimulation, kinase-active SFKs in the nucleus can play an important role in dynamic changes of chromatin structure. The present inventors have found that growth factor stimulation can increase euchromatic hypocondensation and concomitant heterochromatic hypercondensation in $G_1$ phase, and the levels reach a plateau by 30 min, sustain for at least 5 h and return to the basal levels after 24 h. The present inventors also detected serum-activated SFKs in the nucleus more frequently in the euchromatin areas than the heterochromatin areas. It was also determined that nuclear expression of kinase-active SFKs, but not unrelated Syk kinase, can drastically increase both euchromatinization and heterochromatinization in a manner dependent on the levels of nuclear tyrosine phosphorylation. However, growth factor stimulation does not induce chromatin structural changes in SYF cells lacking SFKs, and reintroduction of one SFK member into SYF cells can, albeit insufficiently, induce chromatin structural changes. These results suggest that nuclear tyrosine phosphorylation by SFKs plays an important role in chromatin structural changes upon growth factor stimulation.

The present invention relates to a number of methods and systems to evaluate chromatin structure in a cell(s), which can involve capturing one or more images of a nucleus of one or more nucleic acid stain treated cells. The stain intensity can be measured such as by quantitating the intensity. The mean and/or standard deviation, for instance of the pixel(s) of the image(s) can be measured or determined. Further, the chromatin structure can be determined by the imaging. For instance, the standard deviation can be used to determine the chromatin structure by way of understanding the level of chromatin condensation. As an example, the present invention relates to a method for evaluating chromatin structure in one or more cells, comprising:

providing a sample of one or more cells;

treating the one or more cells, for instance, with a nucleic acid stain;

capturing an image of a nucleus of one or more of the nucleic acid stain treated cells, wherein the image can comprise a plurality of pixels;

quantitating the stain intensity at each pixel of the plurality of pixels;

calculating the mean and/or standard deviation (SD) values of stain intensity per pixel;

and determining the chromatin structure, for instance, wherein the SD value is indicative of the level of chromatin condensation. The one or more cells can be one or more viable cells or can be one or more eukaryotic cells, or can be one or more mammalian cells, and/or other types of cells or any combination thereof.

A plurality of images can be captured over any period of time. The mean and/or SD values of stain intensity per pixel can be calculated for each image. The changes in SD value over the period of time can be correlated to changes in the chromatin structure, for instance over any period of time. The nucleic acid stain can be a fluorescent stain or other type of stain. The nucleic acid stain can be, for instance, propidium iodide. The method of the present invention can further include treating the cells with RNase before treating with a nucleic acid stain. As an option, the image can be captured utilizing a confocal microscope or other type of microscope or detection device. The sample of one or more cells can comprise a planar section slice. The image can be captured at any resolution, such as one that permits one to understand the stain intensity per pixel, for about a 512×512 pixel resolution. The mean and/or SD values can be calculated from the average of at least two captured images of each nucleus. The image of the nucleus can comprise any amount of pixels, such as 500 pixels or greater, or 1000 pixels or greater, or about 6000 pixels or greater. The method of the present invention can further comprise determining the chromatin structure as one of hypocondensed, moderately condensed, or hypercondensed based upon the mean stain intensity per pixel. The nucleic acid stain can comprise propidium iodide, and/or the mean value of stain intensity per pixel can be in a range of about 2400 to about 3000. Other ranges outside of this range can be used.

The present invention also relates to a method for diagnosis, prognosis, and/or monitoring of a lesion in a subject (in vitro or in vivo) comprising evaluating the chromatin structure in a sample of one or more of the lesion cells from the subject, for instance, using the method(s) of the present invention. The SD value can be indicative of a disease state. The method can further involve evaluating the chromatin structure in a sample of one or more non-lesion cells from the subject and can include comparing the calculated SD value of the one or more lesion cells with the calculated SD value of the one or more non-lesion cells. The method can further comprise comparing the calculated SD value of the one or more lesion cells to a range of previously calculated SD values of the same type of lesion that range along a progression curve from normal tissue to a diseased state. The steps can be repeated any number of times. For instance, the steps can be repeated after a predetermined time has elapsed to determine whether the lesion has progressed toward or regressed away from a diseased state. The progression of the lesion (e.g., during the predetermined time) can be utilized to measure the efficacy of a method for treating the lesion. The present invention can relate to a method for diagnosis, prognosis, and/or monitoring of cancer in a subject (in vivo or in vitro) comprising evaluating the chromatin structure in a sample of the one or more cancerous cells from the subject according to the present invention, wherein the SD value can be indicative of a malignant disease or condition. The method can further comprise evaluating the chromatin structure in a sample of one or more non-cancerous cells from the subject according to the present invention, and optionally comparing the calculated SD value of the one or more cancerous cells with the calculated SD value of the one or more non-cancerous cells. The method can further comprise comparing the calculated SD value of the one or more cancerous cells to a range of previously calculated SD values of the same type of cancer that range along a progression curve from normal tissue to malignant disease. The steps can be repeated any number of times. The steps can be repeated after a predetermined time has elapsed to determine whether the cancer has progressed toward or regressed away from malignant disease.

The present invention can also relate to a method of screening (or determining) for a compound that modulates the chromatin structure of one or more cells. The method can include:

contacting the one or more cells with the compound;

evaluating the chromatin structure in the one or more cells according to the methods described herein; and comparing the SD value of the one or more cells contacted with the compound to the SD value of one or more control cells. The compound can stimulate mitotic progression of the one or more cells. The compound can induce apoptosis in the one or more cells. The compound can comprise a growth factor.

The present invention also relates to a system for evaluating the chromatin structure in one or more cells. The system can comprise:

an optical device (or other device) for capturing at least one image of a nucleus of one or more nucleic acid stain treated cells;

a spectrometer device (or other device) for quantitating the stain intensity at each pixel of the image, the spectrometer device optically connected to the optical device and operably connected to a calculating device; and optionally a calculating device for calculating the mean and standard deviation (SD) values of stain intensity per pixel; and optionally a display device for displaying the calculated mean and SD values. The optical device can comprise a confocal microscope. The spectrometer device can detect light emitted by propidium iodide or other compound.

EXAMPLES

The present invention can be even more fully understood with reference to the examples and resulting data that follows.

Materials and Methods

Plasmids cDNA encoding human wild-type c-Src (c-Src-wt, 1-536; with 1 designating the initiator methionine) ([24]; provided by D. J. Fujita) was subcloned into the pcDNA4/TO vector (Invitrogen), as described [7]. Src-HA (1-532), which is tagged with the HA epitope at the C-terminus, was constructed by subcloning c-Src-wt cDNA into the pMH vector (Roche). cDNA encoding human wild-type Lyn (Lyn-wt) was provided by T. Yamamoto (1-512; [25]). The HA-tagged Lyn constructs lacking the C-terminal negative-regulatory tail, Lyn-HA (1-506; kinase-active), and Lyn(K275A)-HA (1-506; kinase-dead), were described previously [5]. cDNA encoding human wild-type Fyn (1-537; [26]), and human wild-type c-Yes (1-543; [27]) (provided by T. Yamamoto) were tagged with the HA epitope at C-terminus. The HA-tagged constructs lacking the C-terminal negative-regulatory tail, Fyn-HA (1-524; kinase-active), and Yes-HA (1-530; kinase-active), were constructed by subcloning into pMH. cDNA encoding human wild-type Syk (1-635; [28]) (provided by E. A. Clark) was subcloned into pcDNA4/TO. To introduce a nuclear localization signal (NLS) [29] into N-termini of constructs, the pcDNA4/TO-NLS-mcs vector was constructed by replacement of the BalI-BssHII fragment of pcDNA4/TO encoding NLS-Chk(PTK)-FLAG [30] with EcoRV-BssHII fragment of pcDNA4/TO vector. The NLS was added to the N-termini of Src-HA, Lyn-HA, Lyn (K275A)-HA, Fyn-HA, Yes-HA, and Syk in pcDNA4/TO-NLS-mcs. NLS-fused green fluorescent protein (NLS-GFP) was constructed as described previously and was subcloned into pcDNA4/TO [30, 31]. pcDNA3/Flag-Suv39h1 and pcDNA3/Flag-G9a were provided by M. Nakao and Y. Shinkai [32]. cDNA encoding human CD25 was provided by A. Iwama [33]. CD25-Lyn-HA was constructed by fusion with CD25 (1-270) at the N terminus of Lyn-HA, and the sequence of SEQ ID NO: 1 (I-P-E-F-P-R-D-P-L-C-W-T-R-P-A-A-P-K-L-S-P-R-A-G-N was inserted between CD25 and Lyn-HA).

Antibodies

The following antibodies were used: phosphotyrosine (pTyr) (4G10 and polyclonal antibody: Upstate Biotechnology, Inc; provided by T. Tamura and T. Yoshimoto [34]), HA epitope (F-7 and Y-11; Santa Cruz Biotechnology, and 12CA5), Flag epitope (M2; Sigma), Src (GD11; Upstate Biotechnology, Inc.), Lyn (Lyn44; Santa Cruz Biotechnology), Yes (Yes1; BD PharMingen), Fyn (Fyn-3; Santa Cruz Biotechnology), Src[pY$^{418}$] (phospho-Src-family; Cell Signaling Technology), lamin B1 (L-5; Zymed), Syk (4D10; Santa Cruz Biotechnology), galactosyltransferase (GalT) ([35]; provided by M. N. Fukuda), desmoglein (clone 62; BD Transduction Laboratories), actin (clone C4; CHEMICON International), cytoplasmic phospholipase $A_2\alpha$ ($cPLA_2\alpha$) (4-4B-3C; Santa Cruz Biotechnology; provided by T. Murayama [36]), histone H3 trimethylated on lysine 4 (histone H3K4me3) (ab1012 and ab8580; Abcam), heterochromatin protein-1α (HP1α) (MAB3446; CHEMICON International), phospho-ATF-2 (phosphothreonine 69 and phosphothreonine 71, ATF-2 pT69/71) (ATF-22P; Sigma), and phospho-histone H3 (Ser10) (phospho-histone H3S10) (6G3; Cell Signaling Technology). Horseradish peroxidase (HRP)-F(ab')$_2$ secondary antibodies were purchased from Amersham Bioscience. FITC-F(ab')$_2$ of IgG or TRITC-IgG secondary antibodies were from BioSource International and Sigma-Aldrich.

Cells and Transfection

COS-1, HeLa cells (Japanese Collection of Research Bioresources, Osaka), MCF-7 (provided by H. Saya), A431 (provided by M. N. Fukuda), HEK293 (provided by M. Tagawa), HCT116 (provided by T. Tomonaga), and SYF ([37]; provided by M. Okada and S. Nada) cells were cultured in Iscove's modified DME containing 5% fetal bovine serum (FBS). Cells were transiently transfected with 0.5 μg of plasmid vector using Trans IT Transfection reagent (Mirus) [16] or with 1 μg of plasmid vector using linear polyethylenimine (25 kDa) (Polyscience, Inc.) [38]. For growth factor stimulation, COS-1 cells were starved under low serum conditions (0.05% FBS) for 24 h and restimulated with serum (5% FBS). For stimulation of endogenous SFKs, cells were treated with 3 mM $Na_3VO_4$ for 3 h, and SFK-mediated tyrosine phosphorylation was verified by treatment with 10 μM PP2 (SFK inhibitor; Calbiochem) or 100 nM wortmannin (PI3K inhibitor; Alomone Labs) for 21 h before $Na_3VO_4$ treatment. $Na_3VO_4$ was dissolved at 500 mM in 500 mM unbuffered HEPES before use. For preparation of stable transfectant clones, SYF cells transfected with c-Src-wt or Lyn-wt were selected in 333 µg/mL Zeocin (Invitrogen), and COS-1 cells were transfected with the BOSH2BGFP-N1 vector, which encodes GFP-tagged histone H2B ([39, 40]; provided by H. Saya), were selected in 3 µg/mL blasticidin.

Purification of Nuclei

Nuclei were prepared as described previously [41]. In brief, COS-1 and HeLa cells were swollen in hypotonic buffer (10 mM HEPES-KOH, pH 7.9, 1.5 mM $MgCl_2$, 10 mM KCl, 0.5 mM DTT, and 1 mM $Na_3VO_4$) containing protease inhibitors (2 mM phenylmethylsulfonyl fluoride, 50 µg/mL aprotinin, 100 µM leupeptin, and 25 µM pepstatin A) at 4° C. for 20 min, followed by homogenization with 20 strokes in a tight-fitting 1-ml Dounce homogenizer. After cell suspension was centrifuged at 200×g for 5 min, cell pellets were resuspended in 0.25 M sucrose containing protease inhibitors, 10 mM $MgCl_2$, and 1 mM $Na_3VO_4$. The resultant suspension was loaded on the top of a 0.35 M sucrose layer containing protease inhibitors, 0.5 mM $MgCl_2$, and 1 mM $Na_3VO_4$ and centrifuged at 1,640×g for 5 min. Pellets were washed with hypotonic buffer, centrifuged at 200×g for 5 min, and solubilized in SDS-sample buffer.

Immunofluorescence

Confocal and Nomarski differential-interference-contrast images were obtained using a Fluoview FV500 confocal laser scanning microscope with a 40×1.00 NA oil and a 100×1.35 NA oil immersion objective (Olympus, Tokyo) and an LSM 510 confocal laser scanning microscope with a 63×1.40 NA oil immersion objective (Zeiss), as described [7, 8, 16, 30, 42, 43]. One planar (xy) section slice (0.6-µm thickness) is shown in all experiments. In brief, cells were fixed with 4% paraformaldehyde for 20 min, and permeabilized in phosphate-buffered saline (PBS) containing 0.1% saponin and 3% bovine serum albumin at room temperature [35]. Cells were subsequently reacted with an appropriate primary antibody for 1 h, washed with PBS containing 0.1% saponin, stained with FITC- or TRITC-conjugated secondary antibody for 1 h. For DNA staining, cells were subsequently treated with 200 µg/ml RNase A for 1 h and 20 µg/ml propidium iodide (PI) for 30 min, and mounted with Prolong Antifade™ reagent (Molecular Probes). To ensure no bleed-through from the fluorescein signal into the red channel, fluorescein and rhodamine were independently excited at 488 nm and 543 nm, respectively. PI was excited at 488 or 543 nm. Emission signals were detected between 505 and 525 nm for fluorescein, at more than 560 nm for rhodamine and more than 610 nm for PI [44]. Composite figures were prepared using Photoshop 5.0 and Illustrator 9.0 software (Adobe). For nuclear staining with anti-pTyr, anti-ATF-2 pT69/71, and anti-histone H3K4me3 antibodies, cells were in situ extracted with 0.5% Triton X-100 at 4° C. for 3 min before fixation with 4% paraformaldehyde [31]. For HP1α staining, cells were fixed in 100% methanol at −20° C. for 10 min followed by permeabilization for 30 min in PBS containing 0.1% Triton X-100 at room temperature. Cells were reacted with anti-HP1α antibody for 1 h at room temperature, washed with PBS four times, and stained with secondary antibody for 1 h [45]. Fluorescence intensity plots of anti-histone H3K4me3, anti-ATF-2 pT69/71 and anti-HP1α antibody and PI staining (see FIGS. 18B, 19B, and 20B, respectively) were generated using Fluoview version 4.3 software (Olympus, Tokyo). For detection of the kinase activity of nuclear SFKs, purified nuclei suspended in kinase buffer (50 mM HEPES-NaOH, pH7.4, 5 mM $MgCl_2$, 5 mM $MnCl_2$ and 0.1 mM $Na_3VO_4$) were preincubated with or without 10 µM PP2 at 30° C. for 30 min, and subsequently incubated with 5 or 10 µM ATP at 30° C. for 30 min, followed by cytocentrifugation at 200×g for 5 min and fixation with 4% paraformaldehyde. DNA was stained with 20 µg/mL PI and 200 µg/mL RNase A for 30 min. Mean fluorescence intensity of tyrosine-phosphorylated proteins in the nucleus was measured using the ImageJ software (National Institutes of Health).

Quantitation of Chromatin Condensation Levels

Figure 57:
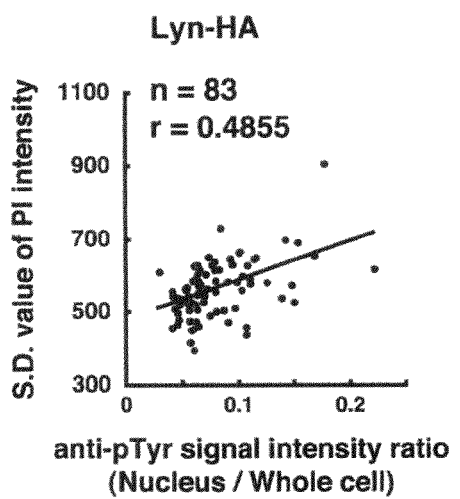
FIG. 57 shows 2D-plot analyses shown with S.D. value of PI intensity (vertical axis) versus mean fluorescence intensity ratios of anti-pTyr staining between the nucleus and the corresponding whole cell (horizontal axis).
Figure 58:
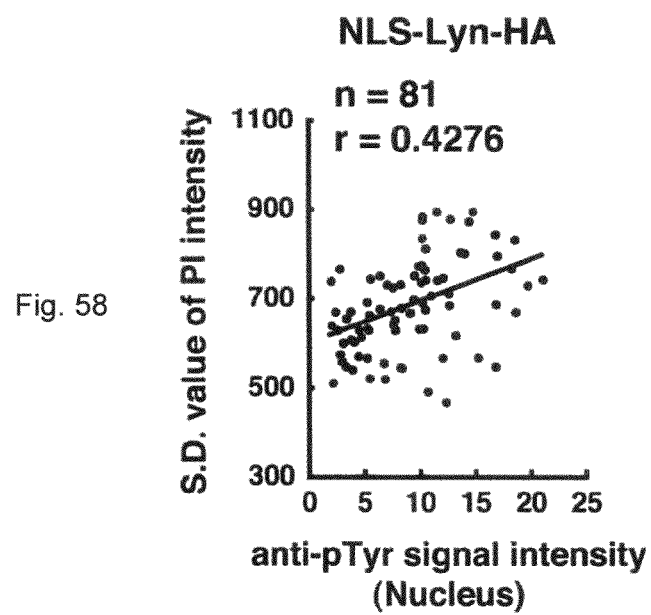
FIG. 58 shows 2D-plot analyses shown with S.D. value of PI intensity (vertical axis) versus mean fluorescence intensity of anti-pTyr staining in the nucleus (horizontal axis).
Figure 59A:
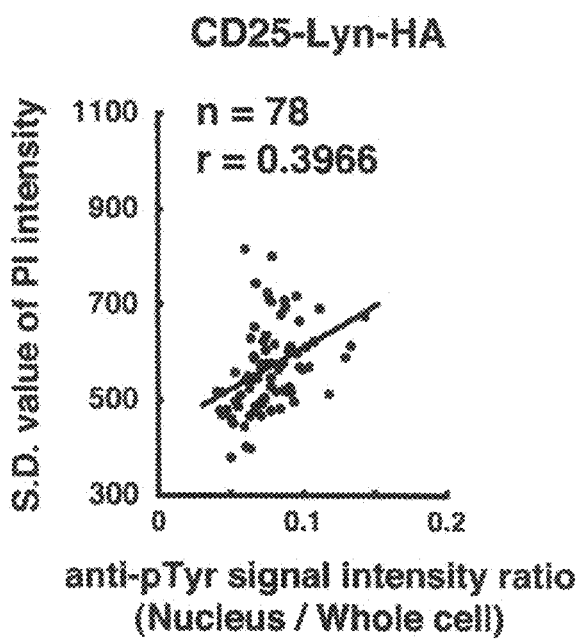
FIG. 59A shows 2D-plot analyses shown with S.D. value of PI intensity (vertical axis) versus ratios of mean fluorescence intensity of anti-pTyr staining between the nucleus and the corresponding whole cell (horizontal axis) in CD25-Lyn-HA-transfected cells.
Figure 59B:
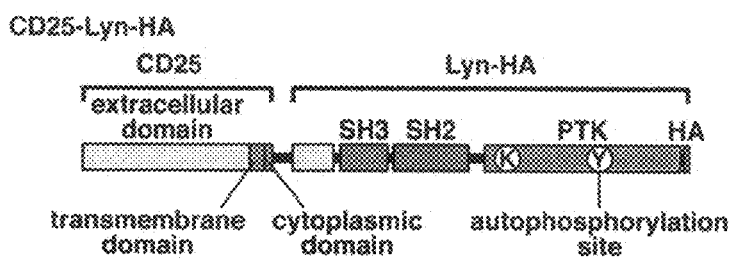
FIG. 59B shows a schematic representation of CD25-Lyn-HA.
Figure 60:
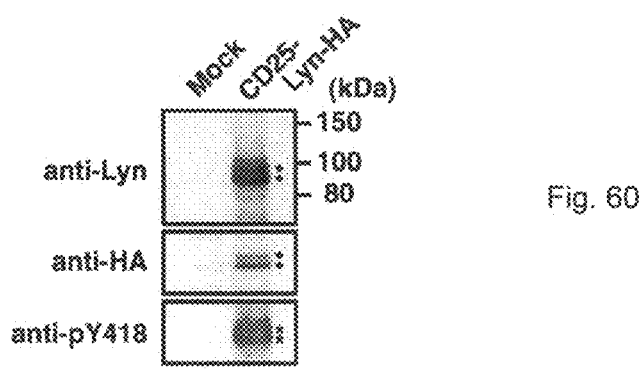
FIG. 60 shows results of Western blotting for whole cell lysates prepared from COS-1 cells transfected with CD25-Lyn-HA.

Confocal images of PI-stained nuclei were obtained as described above. A profile displayed at 512×512 pixel resolution was taken from the average of five scans at the same focal plane. Thickness of one planar (xy) section slice was 0.6 µm and a single nucleus contains 6,000~10,000 pixels. PI fluorescence intensity of each pixel was quantitated, and histograms of fluorescence intensity per pixel for individual nuclei were generated using Fluoview version 4.3 software (Olympus, Tokyo). A single hypocondensed chromatin area usually includes more than 200 pixels. Background levels of fluorescence intensity per pixel were within ranges from 0 to 700. Mean and S.D. values of fluorescence intensity per pixel were calculated from all pixels that occupy the nucleus in each cell. The level of chromatin condensation was represented by the S.D. value for each cell under conditions where the mean value of fluorescence intensity per pixel for each cell ranges between 2400 and 3000. Two-dimensional (2D) isometric intensity profiles (image resolution: 70×70 pixels) of PI staining were generated using Fluoview version 4.3 (Olympus, Tokyo) and Microsoft Excel 2004 software. Nuclei were divided into approximately 3,000 pixels, and one displayed pixel contained 2-3 pixels that were used for quantitation of means and S.D. values. FIGS. 1A, 1B, 1C through FIGS. 6A, 6B, 6C show means and S.D. values for each displayed pixel of a P.I. stained nucleus, as well as the corresponding histogram and 2D isometric intensity profiles of the P.I. staining. 2D-plot analyses of S.D. value of PI intensity versus mean fluorescence intensity of anti-pTyr or anti-HA staining or GFP within individual nuclei as shown in FIGS. 41, 42 62 and 63) and 2D-plot analyses generated using Fluoview version 4.3 software, of S.D. value of PI intensity versus (a) ratio of integrated fluorescence intensity of anti-pTyr staining in the nucleus to that in the corresponding whole cell (Nucleus/Whole cell), are shown in FIGS. 57 and 59A and (b) integrated fluorescence intensity of anti-pTyr staining in the nucleus is shown in FIG. 58.

Cell Cycle Analysis

To obtain S- and $G_2$-phase cells, COS-1 cells grown in Iscove's modified DME containing 5% FBS were blocked at S phase by exposure to 3 mM thymidine for 18 h. Cells were washed free of thymidine with PBS, and cultured for further 2 or 5 h. Cells were detached by trypsinization, fixed in 1.5% paraformaldehyde at 4° C. for 1 h, and then permeabilized with 70% ethanol at −30° C. for more than 1 h. Fixed cells were washed twice with PBS containing 3% FBS, and treated with 200 µg/ml RNase A and 50 µg/ml PI at 37° C. for 30 min to stain DNA. Cell cycle phase was analyzed by flow cytometry using a MoFlo cell sorter equipped with a 488-nm argon laser (Beckman Coulter). Cells transfected with Lyn-HA or NLS-Lyn-HA were cultured for 36 h, fixed and permeabilized as described above. Fixed cells were washed with PBS containing 3% FBS, stained with anti-HA antibody for 1 h, washed with PBS and stained with FITC-conjugated secondary antibody for 1 h. After DNA staining with PI as described above, cell cycle phase was analyzed in cells expressing Lyn-HA or NLS-Lyn-HA.

Western Blotting

Western blotting was performed with enhanced chemiluminescence (Amersham Bioscience) as described previously

[5, 16, 46]. Lysates of whole cells or purified nuclei prepared in SDS-sample buffer were subjected to SDS-polyacrylamide gel electrophoresis and electrotransferred onto polyvinylidene difluoride membranes. Protein bands were detected with appropriate antibodies and analyzed with the Image Gauge software using an Image Analyzer LAS-1000plus (Fujifilm, Tokyo). Sequential reprobing of membranes with a variety of antibodies was performed after the complete removal of primary antibodies from membranes in stripping buffer or inactivation of HRP by 0.1% $NaN_3$, according to the manufacturer's instructions. Composite figures were prepared using Photoshop 5.0 and Illustrator 9.0 software (Adobe).

Results

Quantitation of Chromatin Structural Change

Figures 7A, 7B, 7C:
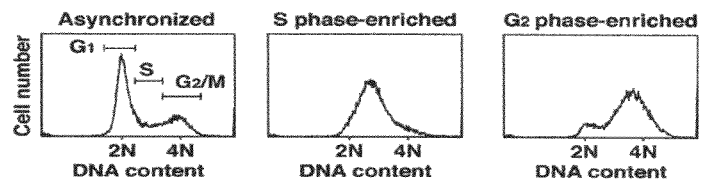
FIG. 7A shows a histogram depicting DNA content for asynchronized cell populations.
FIG. 7B shows a histogram depicting DNA content for S phase-enriched cell populations.
FIG. 7C shows a histogram depicting DNA content for $G_2$ phase-enriched cell populations.
Figure 8:
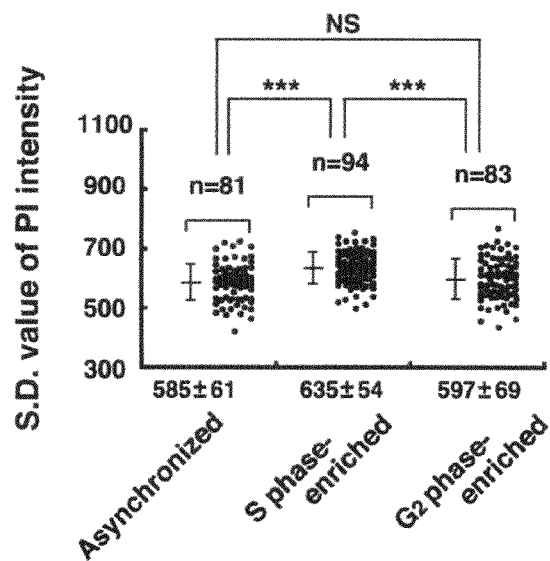
FIG. 8 shows a plot representing each S.D. value of PI intensity per pixel for each cell, and bars and values represent means±S.D. from a representative experiment.
Figure 9:
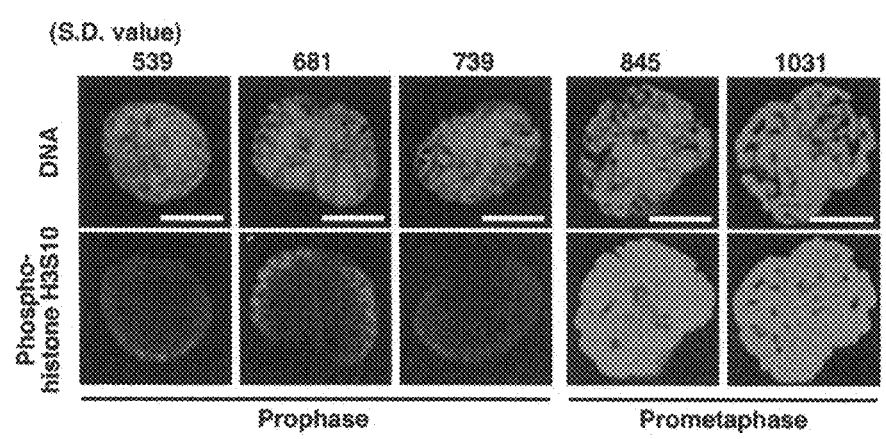
FIG. 9 shows fluorescence imaging of cells stained with anti-phospho-histone H3S10 antibody and PI.
Figure 10:
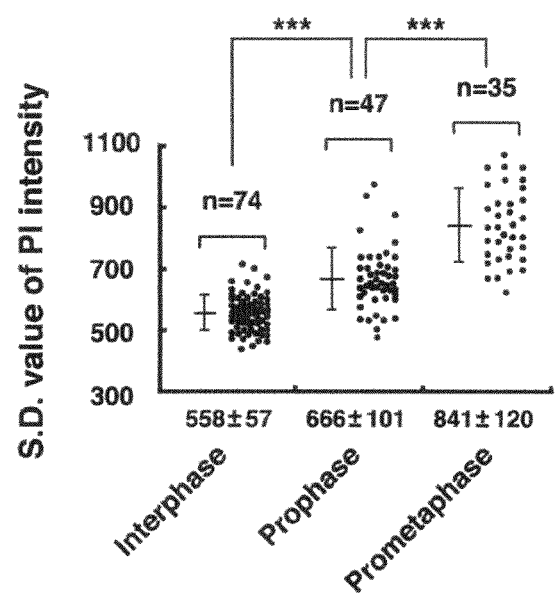
FIG. 10 shows a plot in representing each S.D. value of PI intensity per pixel for each cell, and bars and values represent means±S.D. from a representative experiment.
Figures 11A, 11B, 11C, 11D:
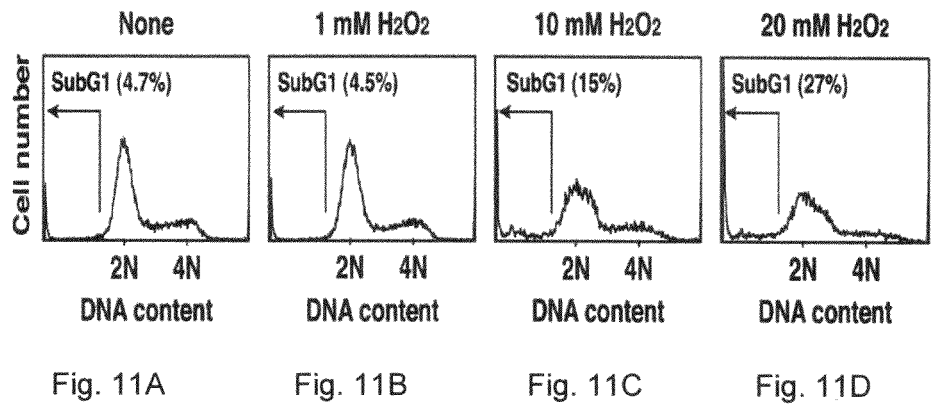
FIGS. 11A-11D show histograms depicting DNA content for COS-1 cells treated for 1 h with $H_2O_2$ at the indicated concentrations and stained with PI for DNA.
Figure 12:
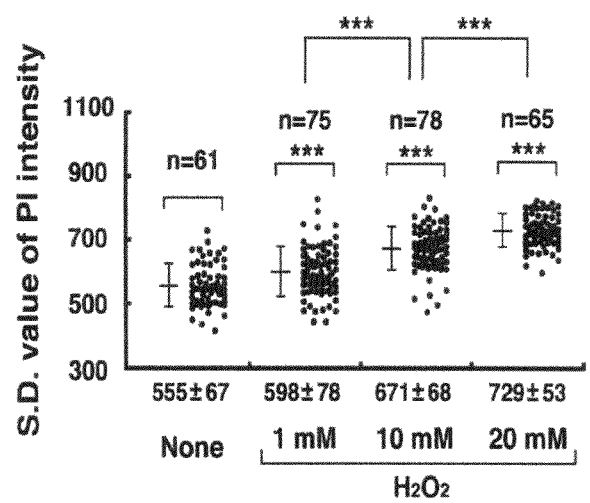
FIG. 12 shows a plot representing each S.D. value of PI intensity per pixel for each cell, and bars and values representing means±S.D. from a representative experiment.
Figure 13:
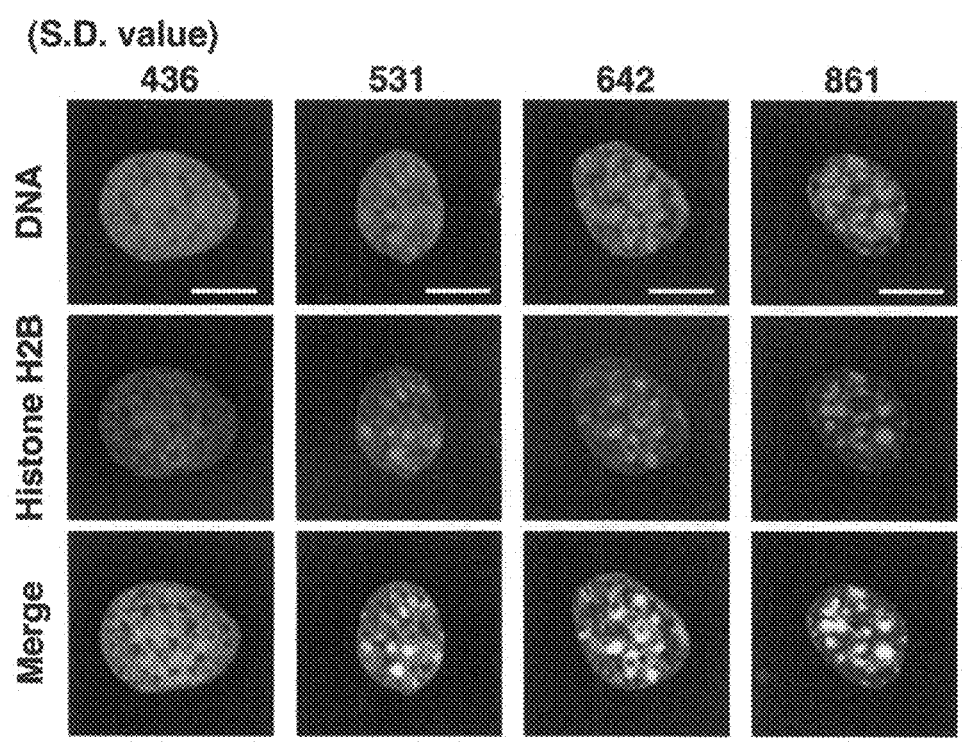
FIG. 13 shows fluorescence images of DNA and histone H2B-GFP staining.

FIGS. 1A, 2A, 3A, 4A, 5A, and 6A show DNA fluorescence images obtained with propidium iodide (PI) staining. Images were equally divided into a large number of pixels as described under 'Materials and methods'. Fluorescence intensity of each pixel was measured, and mean intensity and S.D. value were calculated for each cell. Scale bars, 10 µm. Histograms shown in FIGS. 1B, 2B, 3B, 4B, 5B, and 6B represent the areas of hypocondensed DNA (700≤fluorescence intensity per pixel<2200, green), moderately condensed DNA (2200≤fluorescence intensity per pixel≤3200, yellow), hypercondensed DNA (fluorescence intensity per pixel, >3200, red), and background (fluorescence intensity per pixel<700, blue). 2D isometric intensity profiles are shown in FIGS. 1C, 2C, 3C, 4C, 5C, and 6C. Spectrum of PI fluorescence intensity shown on the right (from 0 to 4095) represents hypercondensed DNA (red), moderately condensed DNA (yellow), hypocondensed DNA (green), and background (blue). FIGS. 7A-7C and 8 relate to COS-1 cells synchronized in S or $G_2$ phase as described under 'Materials and methods'. DNA contents were analyzed by flow cytometry for asynchronized cells and S phase- and $G_2$ phase-enriched cell populations, and results are shown as histograms in FIGS. 7A-7C, respectively. $G_2$ phase-enriched cell population was obtained from cells that were synchronized in $G_2$ phase. Peaks represent 2N ($G_1$ phase) and 4N ($G_2$ phase) DNA content. The plot depicted in FIG. 8 represents each S.D. value of PI intensity per pixel for each cell, and bars and values represent means±S.D. from a representative experiment (81~94 cells) in three independent experiments. Asterisks indicate significant differences (*p<0.001; NS, not significant) calculated by Student's t-test. FIGS. 9 and 10 relate to COS-1 cells blocked at S phase by exposure to 3 mM thymidine for 18 h, washed free of thymidine, and cultured for further 9 h. Cells were stained with anti-phospho-histone H3S10 antibody and PI for DNA to detect mitotic chromosomes. The S.D. values of PI intensity are shown in FIG. 9. Scale bars, 10 µm. The plot in FIG. 10 represents each S.D. value of PI intensity per pixel for each cell, and bars and values represent means±S.D. from a representative experiment (35~74 cells). Asterisks indicate the significant difference (*p<0.001) calculated by Student's t-test. FIGS. 11A-11D and FIG. 12 relate to COS-1 cells treated for 1 h with $H_2O_2$ at the indicated concentrations and stained with PI for DNA. DNA contents were analyzed by flow cytometry, and results are shown as histograms in FIGS. 11A-11D. The plot in FIG. 12 represents each S.D. value of PI intensity per pixel for each cell, and bars and values represent means±S.D. from a representative experiment (61~78 cells). Asterisks indicate the significant difference (***p<0.001) calculated by Student's t-test. FIG. 13 relates to COS-1 cells stably expressing histone H2B-GFP and stained with PI for DNA. Fluorescence images of DNA and histone H2B-GFP staining are shown in FIG. 13. The S.D. values of PI intensity are shown on top of the images depicted in FIG. 13. Scale bars, 10 µm.

Serum Growth Factor-Induced Changes in Chromatin Structure

Figure 16:
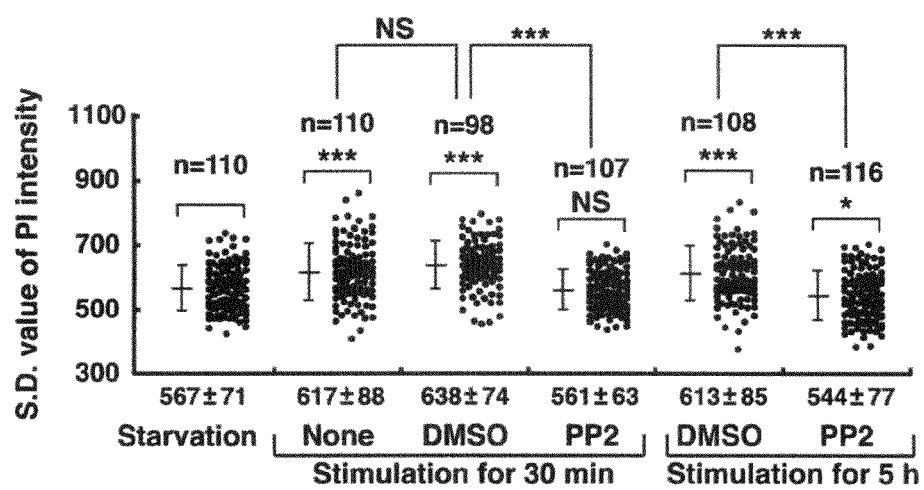
FIG. 16 shows a plot representing each S.D. value of PI intensity per pixel for each cell, and bars and values represent means±S.D. from a representative experiment.
Figure 17A:
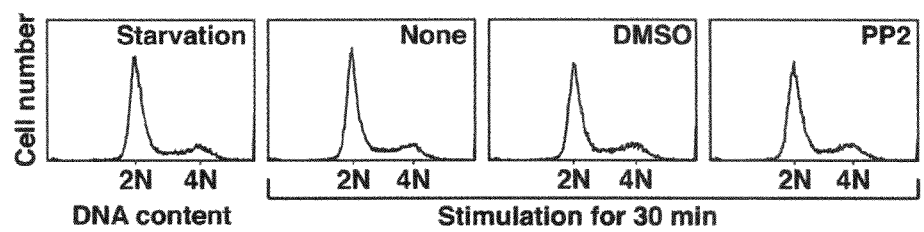
FIGS. 17A and 17B show histograms depicting DNA content for COS-1 cells that were starved for 24 h under low serum conditions (0.05% FBS) and stimulated with serum (5% FBS) for the indicated times, respectively.
Figure 17B:
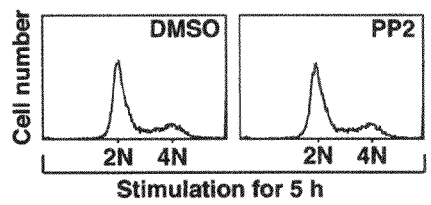
Figures 18A, 18B:
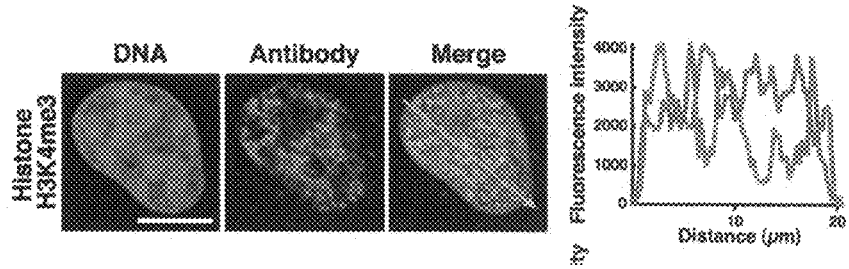
FIG. 18A shows fluorescence images of DNA staining with PI and anti-histone H3K4me3 antibody.
FIG. 18B shows a fluorescence intensity plot for PI and anti-histone H3K4me3 antibody.
Figures 19A, 19B:
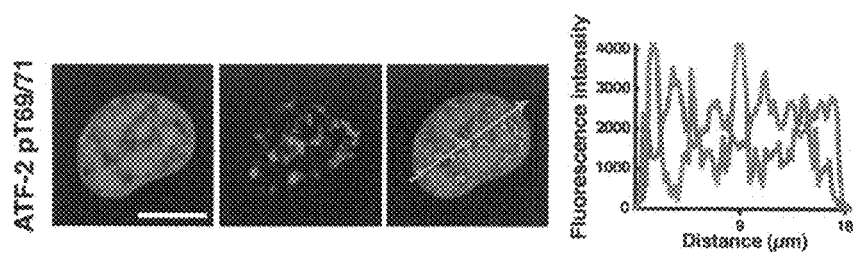
FIG. 19A shows fluorescence images of DNA staining with PI and anti-ATF-2 pT69/71 antibody.
FIG. 19B shows a fluorescence intensity plot for PI and anti-ATF-2 pT69/71 antibody.
Figures 20A, 20B:
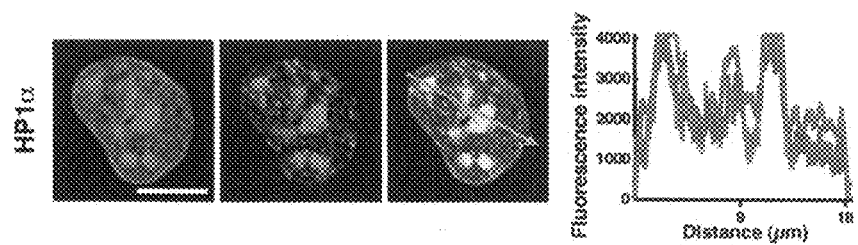
FIG. 20A shows fluorescence images of DNA staining with PI and anti-HP1α antibody.
FIG. 20B shows a fluorescence intensity plot for PI and anti-HP1α antibody.
Figures 21A, 21B:
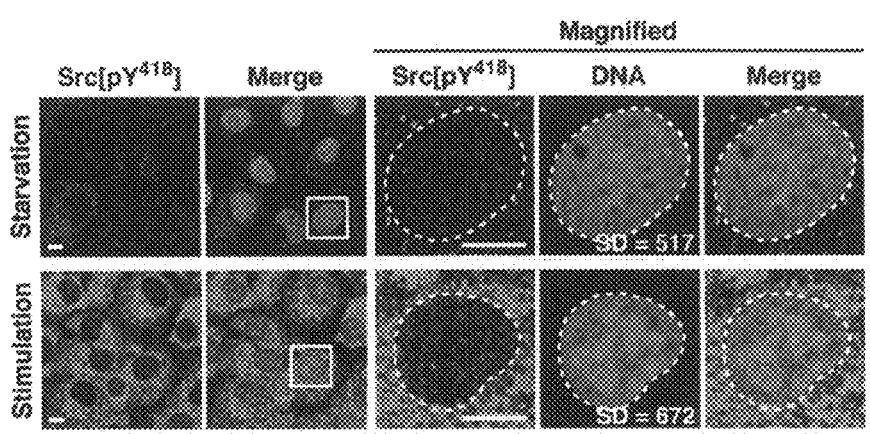
FIG. 21A shows fluorescence images of DNA staining with PI and anti-Src[$pY^{418}$] antibody for serum-starved COS-1 cells.
FIG. 21B shows fluorescence images of DNA staining with PI and anti-Src[$pY^{418}$] antibody for serum-starved COS-1 cells which were stimulated with 5% FBS for 30 min.

COS-1 cells were starved for 24 h under low serum conditions (0.05% FBS), stimulated with serum (5% FBS) for 5 h, and then stained with PI for DNA. Fluorescence images of DNA staining are shown in FIGS. 14A and 14B. The S.D. values of PI intensity are shown at the top of the images depicted in FIGS. 14A and 14B. Scale bars, 10 µm. FIGS. 15 and 16 are graphs quantitating chromatin condensation levels using S.D. values. Serum stimulation in FIGS. 15 and 16 is shown in the presence or absence of 10 µM PP2 for the indicated times. DMSO (dimethyl sulfoxide, solvent control). The plot in FIGS. 15 and 16 represents each S.D. value of PI intensity per pixel for each cell, and bars and values represent means±S.D. from a representative experiment (71~116 cells) in three independent experiments. Asterisks indicate significant differences (*p<0.05; p<0.01; *p<0.001; NS, not significant) between starvation and stimulation calculated by Student's t-test. DNA contents were analyzed by flow cytometry. FIGS. 17A and 17B are histograms showing DNA content. FIGS. 18A-18B, 19A-19B, and 20A-20B relate to serum-starved COS-1 cells that were stimulated with 5% FBS for 5 h and in situ extracted with 0.5% Triton X-100 followed by fixation and doubly staining with PI and anti-histone H3K4me3 or anti-ATF-2 pT69/71 antibody, and serum-stimulated cells that were also fixed in methanol followed by doubly staining with anti-HP1α antibody and PI, as described under 'Materials and methods'. Scale bars, 10 µm. Fluorescence images of the stained cells are shown in FIGS. 18A, 19A, and 20A. Fluorescence intensity plots of anti-histone H3K4me3 antibody, anti-ATF-2 pT69/71 antibody, and anti-HP1α antibody are shown in FIGS. 18B, 19B, and 20B, respectively. Intensity plots along the line drawn in merged images are shown on the right. Red, PI intensity; green, antibody staining intensity. FIGS. 21A and 21B relate to serum-starved COS-1 cells which were stimulated with 5% FBS for 30 min (stimulation), or not (starvation), and doubly stained with anti-Src[$pY^{418}$] antibody and PI. Broken lines indicate outlines of the nucleus. The S.D. values of PI intensity are shown in the DNA images of FIGS. 21A and 21B. Magnified images of the squared areas are shown on the right. Scale bars, 10 µm.

Figure 22:
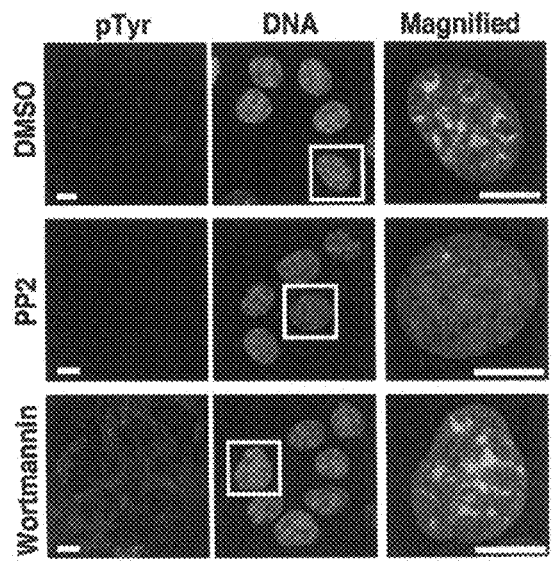
FIG. 22 shows fluorescence images of DNA staining for COS-1 cells that were treated with DMSO, 10 μM PP2, or 100 nM wortmannin for 24 h and doubly stained with anti-pTyr antibody and PI.
Figure 23:
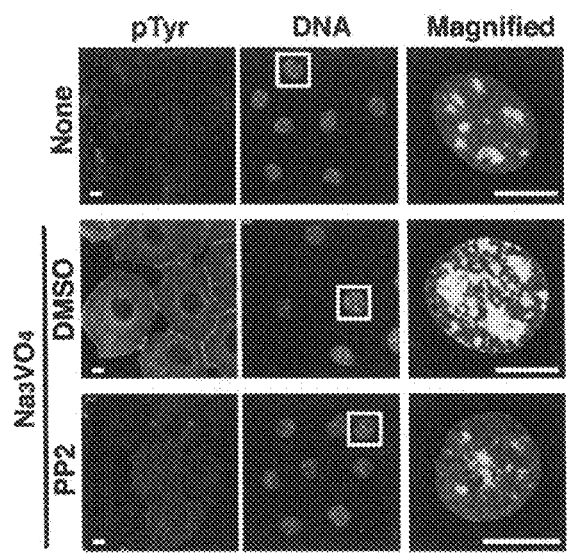
FIG. 23 shows fluorescence images of DNA staining for COS-1 cells that were pretreated with DMSO alone or 10 μM PP2 for 21 h and then incubated with 3 mM sodium orthovanadate ($Na_3VO_4$) for 3 h.
Figure 24:
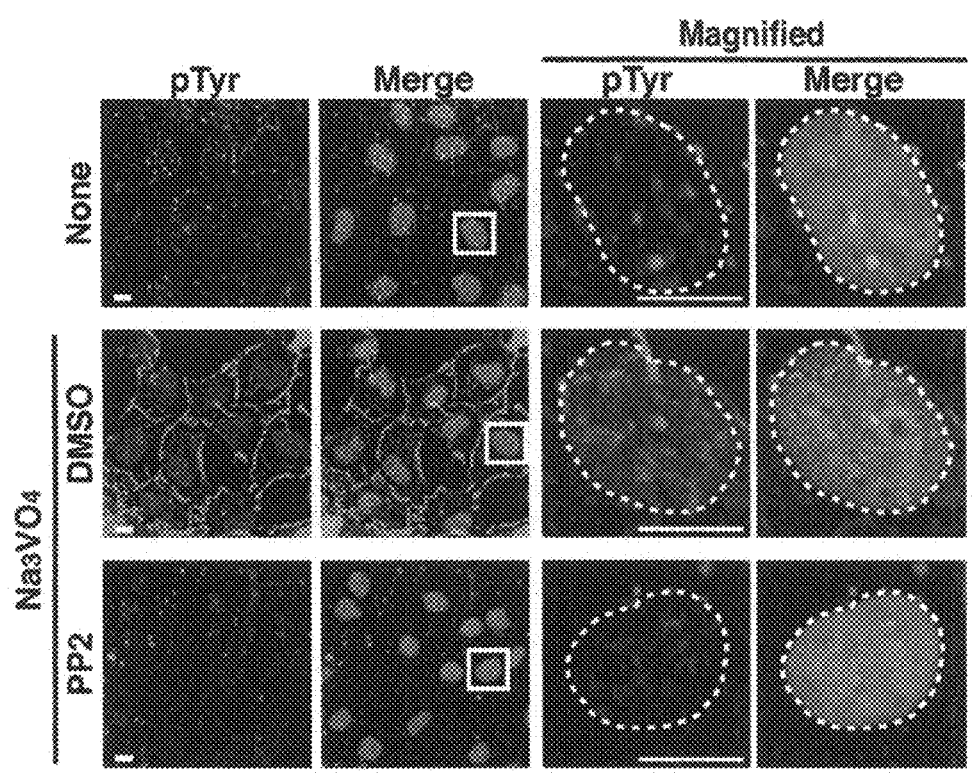
FIG. 24 shows fluorescence images of DNA and pTyr staining for cells that were in situ extracted with 0.5% Triton X-100 followed by fixation and doubly staining with anti-pTyr antibody and PI.
Figure 25:
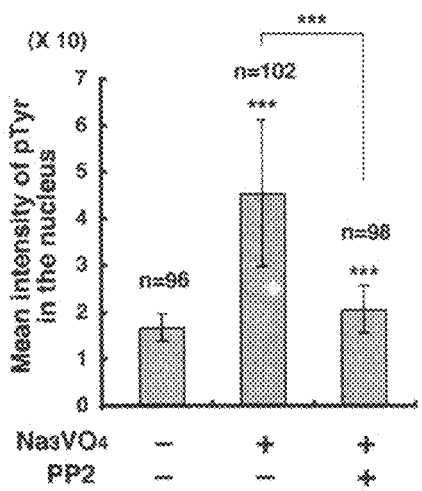
FIG. 25 shows a graph depicting mean fluorescence intensity of anti-pTyr staining in the nucleus that is based on data obtained from the experiments described for FIG. 24.
Figure 26:
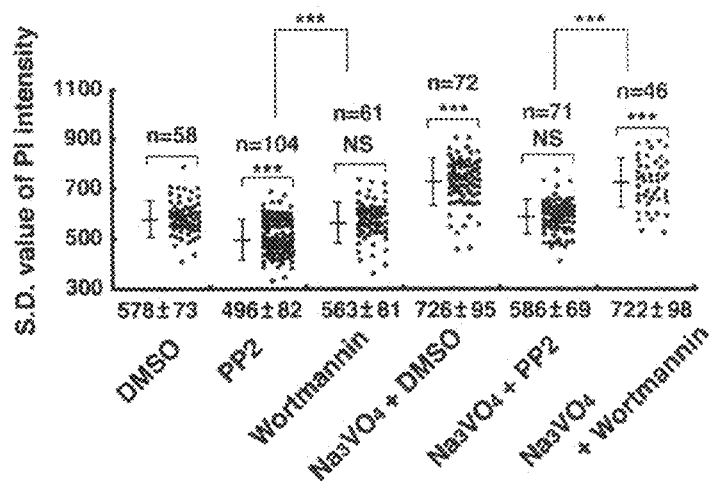
FIG. 26 shows a plot representing each S.D. value of PI intensity per pixel for each cell, and bars and values represent means±S.D. from a representative experiment.
Figures 27A, 27B, 27C, 27D:
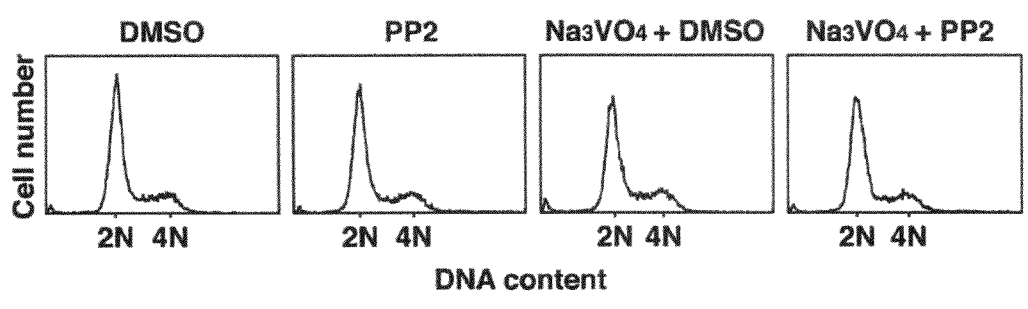
FIGS. 27A-27D show histograms depicting DNA content for COS-1 cells that were treated as indicated.
Figure 28:
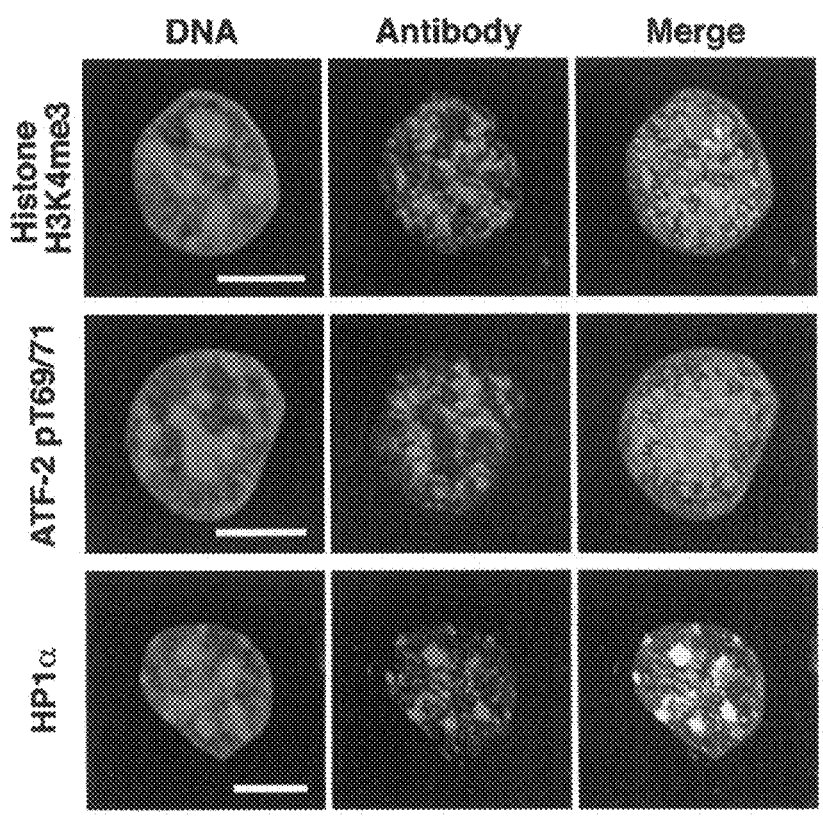
FIG. 28 shows fluorescence images of DNA staining for COS-1 cells that were treated with 3 mM $Na_3VO_4$ for 3 h and doubly stained with PI and anti-histone H3K4me3, anti-ATF-2 pT69/71, or anti-HP1α antibody.

Induction of Chromatin Structural Changes by SFK-Mediated Tyrosine Phosphorylation FIG. 22 relates to COS-1 cells that were treated with DMSO, 10 µM PP2, or 100 nM wortmannin for 24 h and doubly stained with anti-pTyr antibody and PI. Magnified images of the squared areas are shown on the right. Scale bars, 10 µm. FIG. 23 relates to COS-1 cells that were pretreated with DMSO alone or 10 µM PP2 for 21 h and then incubated with 3 mM sodium orthovanadate ($Na_3VO_4$) for 3 h. Tyrosine-phosphorylated proteins and DNA were stained with anti-pTyr antibody and PI. Magnified images of the squared areas are shown on the right. Scale bars, 10 µm. To reduce cytoplasmic tyrosine-phosphorylated proteins, cell were in situ extracted with 0.5% Triton X-100 followed by fixation and doubly staining with anti-pTyr antibody and PI, as described under 'Materials and methods'. Fluorescence images of the stained cells are depicted in FIG. 24. Magnified images of the squared areas are shown on the right. Broken lines indicate outlines of the nucleus. Scale bars, 10 µm. FIG. 25 shows mean fluorescence intensity of anti-pTyr staining in the nucleus that is based on data obtained from the experiments described for FIG. 24, and data represent means±S.D. from a representative experiment (96~102 cells) in at least three independent experiments. Asterisks indicate the significant difference (*p<0.001) calculated by Student's t-test. FIG. 26 relates to COS-1 cells that were treated as the cells described above for FIGS. 1A-8. The levels of chromatin condensation were assessed using S.D. values of PI intensity per pixel. The plot represents each S.D. value of PI intensity per pixel for each cell, and bars and values represent means±S.D. from a representative experiment (46~104 cells) in at least three independent experiments. Asterisks indicate the significant difference (*p<0.001; NS, not significant) calculated by Student's t-test. DNA contents were analyzed by flow cytometry, and results are shown as histograms shown in FIGS. 27A-27D. FIG. 28 relates to COS-1 cells that were treated with 3 mM $Na_3VO_4$ for 3 h and doubly stained with PI and anti-histone H3K4me3, anti-ATF-2 pT69/71, or anti-HP1α antibody, as described under 'Materials and methods'. Scale bars, 10 μm.

Figure 29:
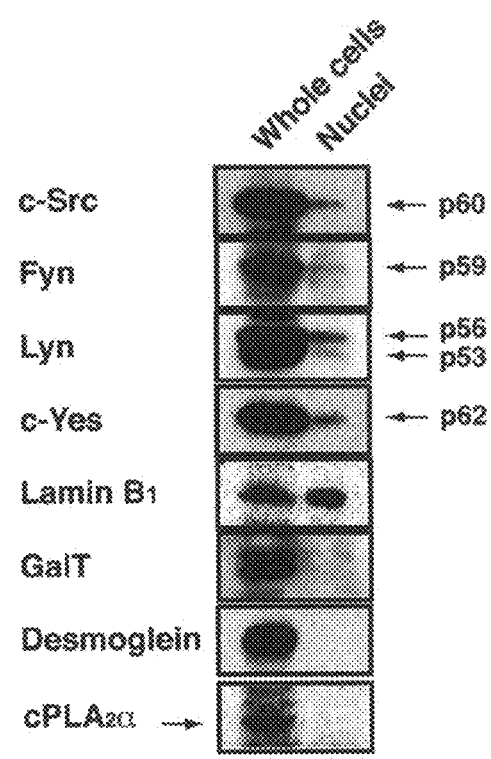
FIG. 29 shows results of Western blotting for purified nuclei prepared from COS-1 cells.
Figure 30:
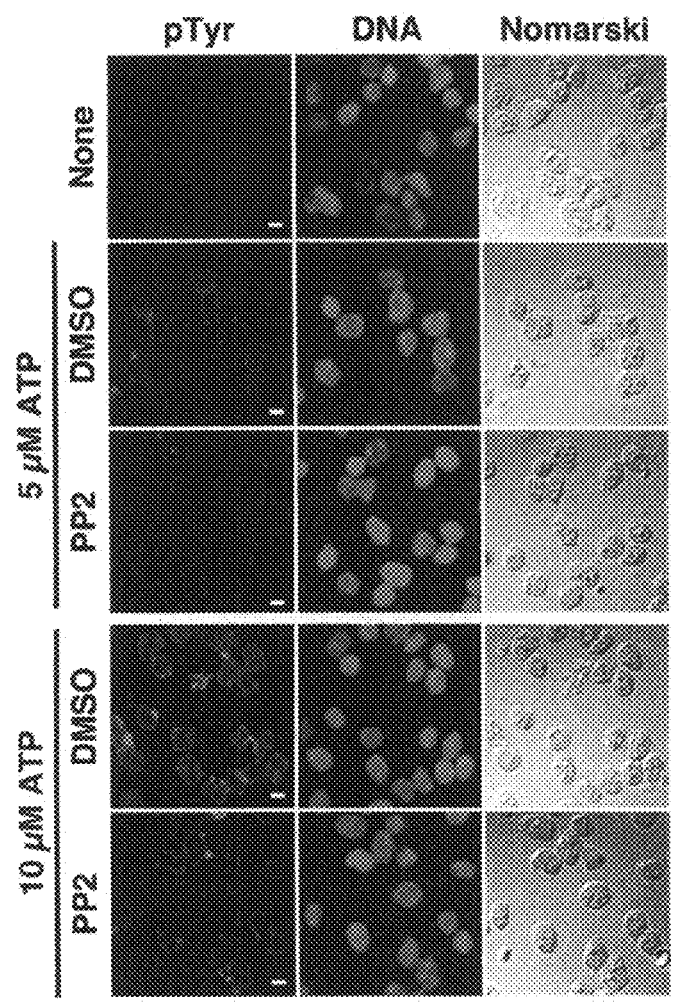
FIG. 30 shows fluorescence images of pTyr and DNA in purified nuclei.
Figure 31:
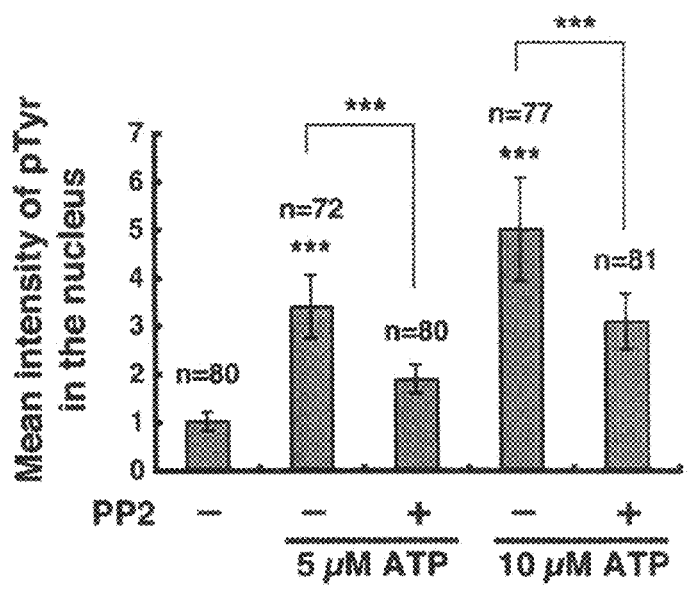
FIG. 31 shows a graph depicting mean fluorescence intensity of anti-pTyr staining in purified nuclei.

Nuclear Localization of SFKs and In Vitro Tyrosine Phosphorylation of Purified Nuclei FIG. 29 shows results of Western blotting for purified nuclei prepared from COS-1 cells as described under 'Materials and methods'. Western blots of lysates from whole cells and purified nuclei were probed with antibodies against individual SFK members, lamin B1, galactosyltransferase (GalT), desmoglein, and cytoplasmic phospholipase $A_2\alpha$ ($cPLA_2\alpha$). FIG. 30 relates to purified nuclei prepared from COS-1 cells were pretreated with DMSO alone or 10 μM PP2 for 30 min and incubated with the indicated concentrations of ATP for 30 min at 30° C. Tyrosine-phosphorylated proteins and DNA were stained with anti-pTyr antibody and PI. Scale bars, 10 μm. FIG. 30 shows fluorescence images of tyrosine-phosphorylation (pTyr) in purified nuclei. FIG. 31 shows mean fluorescence intensity of anti-pTyr staining in purified nuclei, and data represent means±S.D. from a representative experiment (72~81 cells) in at least three independent experiments. Asterisks indicate the significant difference (***p<0.001) calculated by Student's t-test.

Changes in Chromatin Architecture Induced by Nuclear-Targeted SFKs

Figure 32:
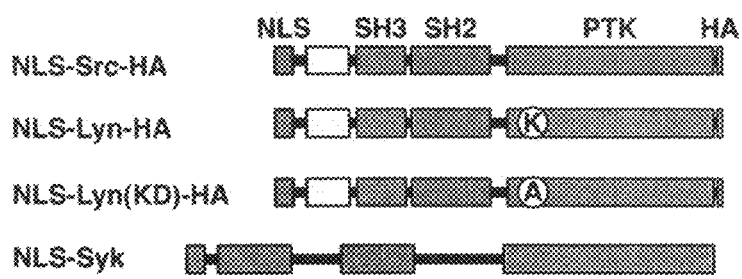
FIG. 32 shows schematic representations of NLS-Src-HA, NLS-Lyn-HA, NLS-Lyn(KD)-HA and NLS-Syk. NLS, nuclear localization signal; SH, Src homology domain; PTK, protein-tyrosine kinase domain; HA, HA-epitope tag; KD, kinase-dead K275A mutation.
Figure 33:
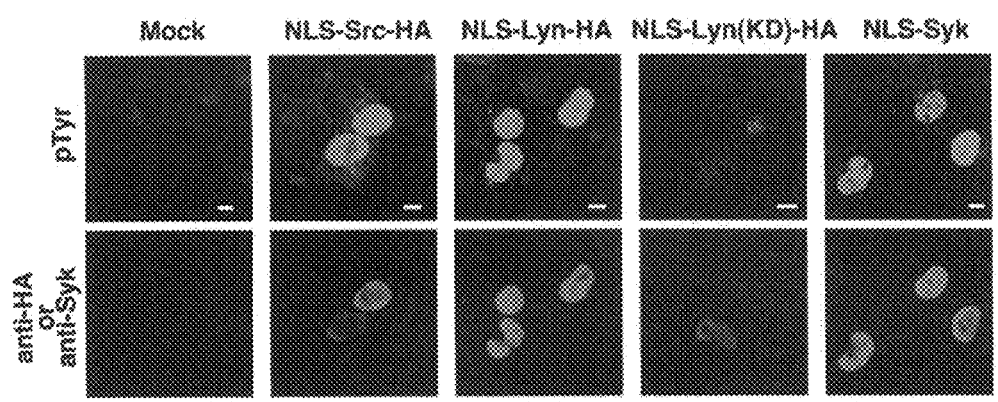
FIG. 33 shows fluorescence images of pTyr staining for COS-1 cells transfected with the indicated construct that were cultured for 36 h and doubly stained with anti-pTyr antibody and anti-HA or anti-Syk antibody.
Figures 34A, 34B:
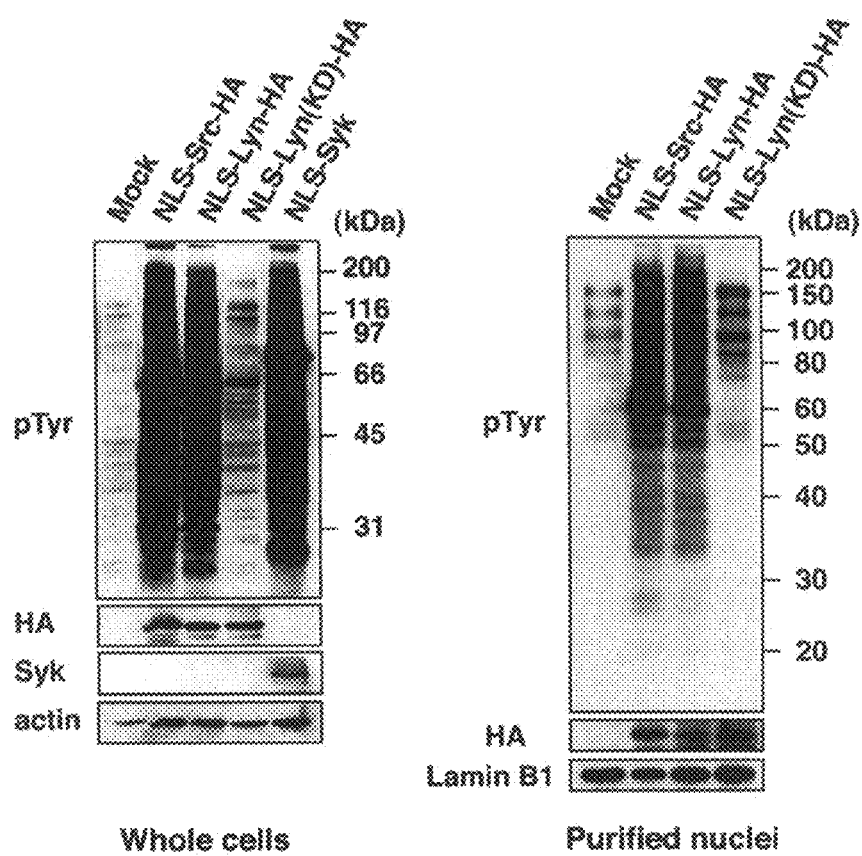
FIGS. 34A and 34B show results of Western blotting for whole cells and purified nuclei prepared from COS-1 transfected with the indicated construct that were cultured for 36 h.
Figure 35:
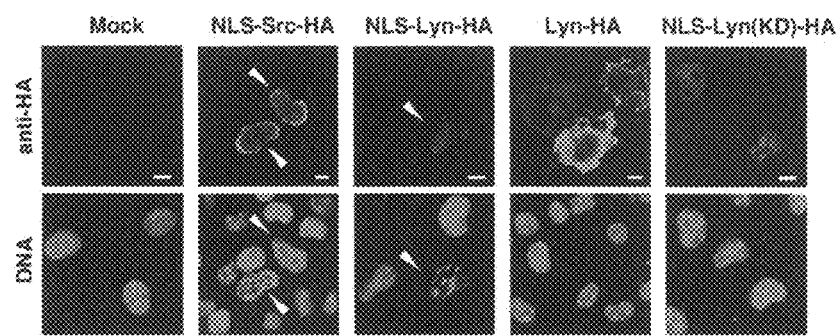
FIG. 35 shows fluorescence images of DNA staining for COS-1 cells transfected with the indicated construct that were cultured for 36 h and doubly stained with PI and anti-HA antibody.
Figure 36:
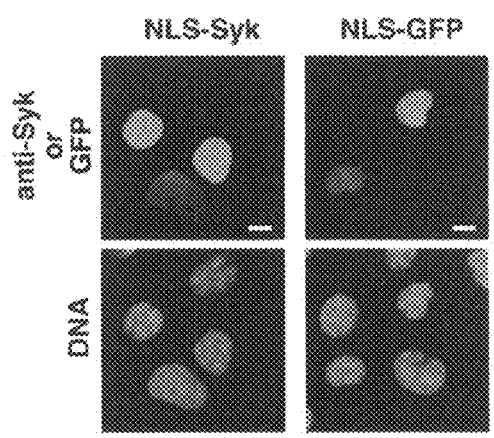
FIG. 36 shows fluorescence images of DNA staining for COS-1 cells transfected with the indicated construct that were cultured for 36 h and doubly stained with PI and anti-Syk antibody or visualized with GFP fluorescence.
Figure 37:
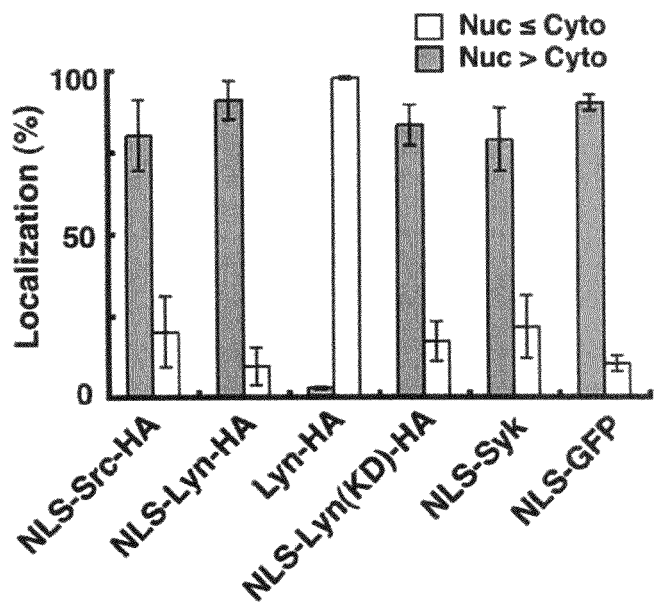
FIG. 37 shows a graph comparing protein expression in the nucleus with protein expression in the cytoplasm.
Figures 38A, 38B, 38C:
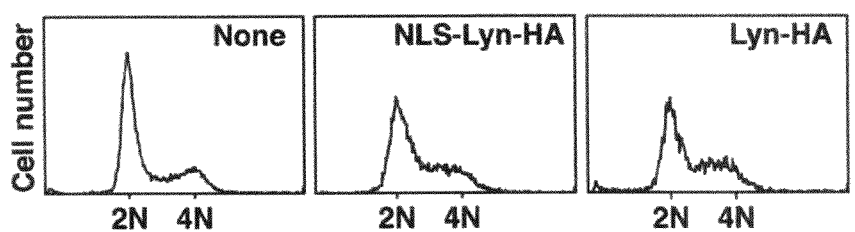
FIGS. 38A-38C show histograms depicting DNA content for COS-1 cells transfected with nothing, Lyn-HA, and NLS-Lyn-HA.
Figure 39:
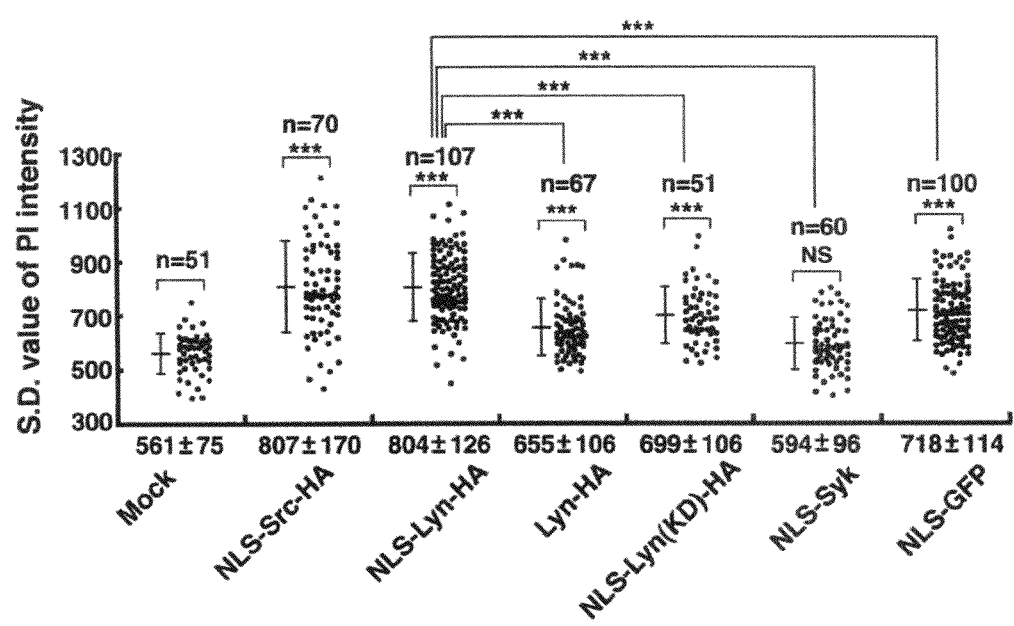
FIG. 39 shows a plot depicting each S.D. value of PI intensity per pixel for each cell, and bars and values represent means±S.D. from a representative experiment.
Figure 40A:
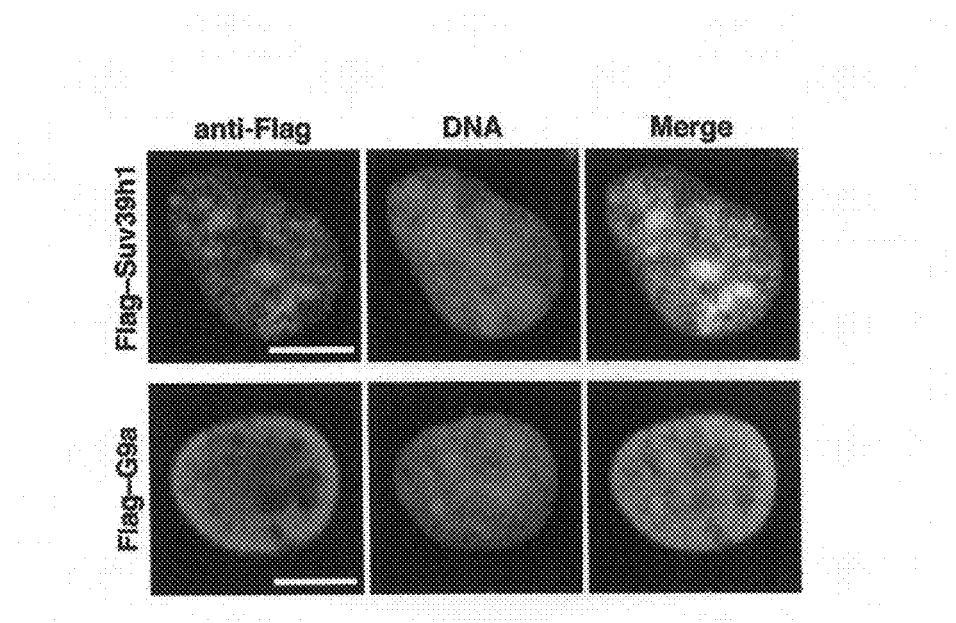
FIG. 40A shows fluorescence images of DNA staining for COS-1 cells transfected with Flag-Suv39h1 or Flag-G9a that were cultured for 36 h and doubly stained with anti-Flag antibody and PI.
Figure 40B:
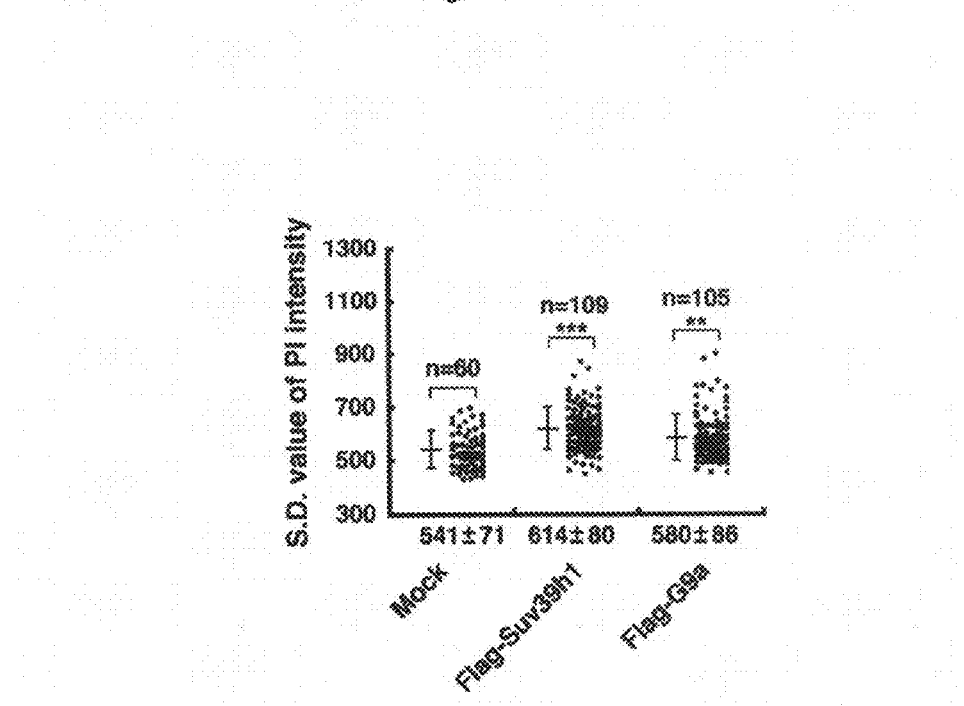
FIG. 40B shows a plot depicting each S.D. value of PI intensity per pixel for each cell.
Figure 43:
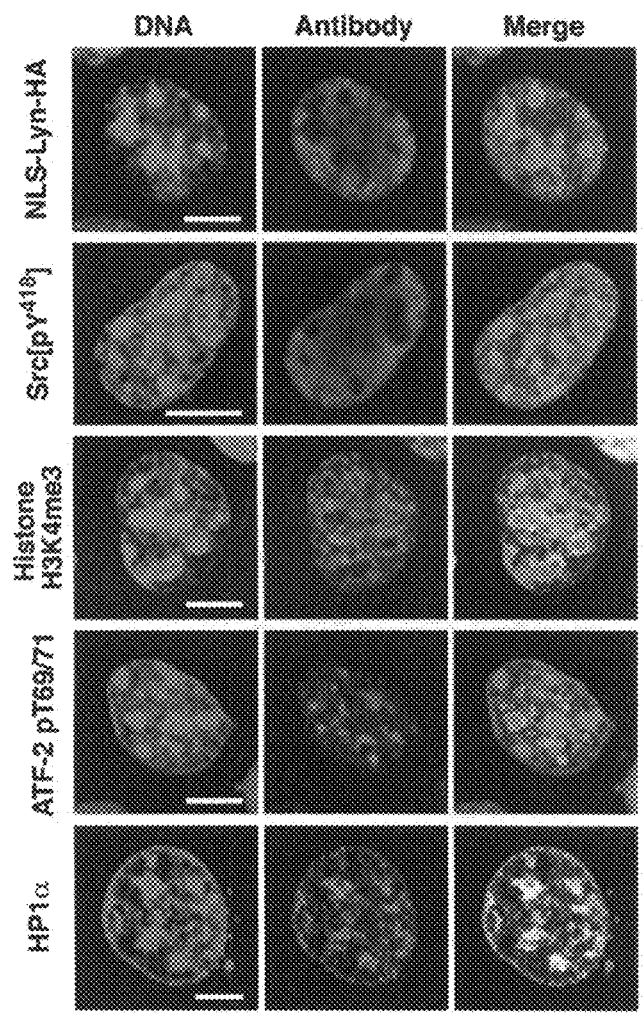
FIG. 43 shows fluorescence images of DNA staining for COS-1 cells transfected with NLS-Lyn-HA that were cultured for 24 h and doubly stained with anti-HA antibody and PI, and NLS-Lyn-HA-transfected cells that were also doubly stained with PI and anti-Src[$pY^{418}$], anti-histone H3K4me3, anti-ATF-2 pT69/71, or anti-HP1α antibody.
Figure 44:
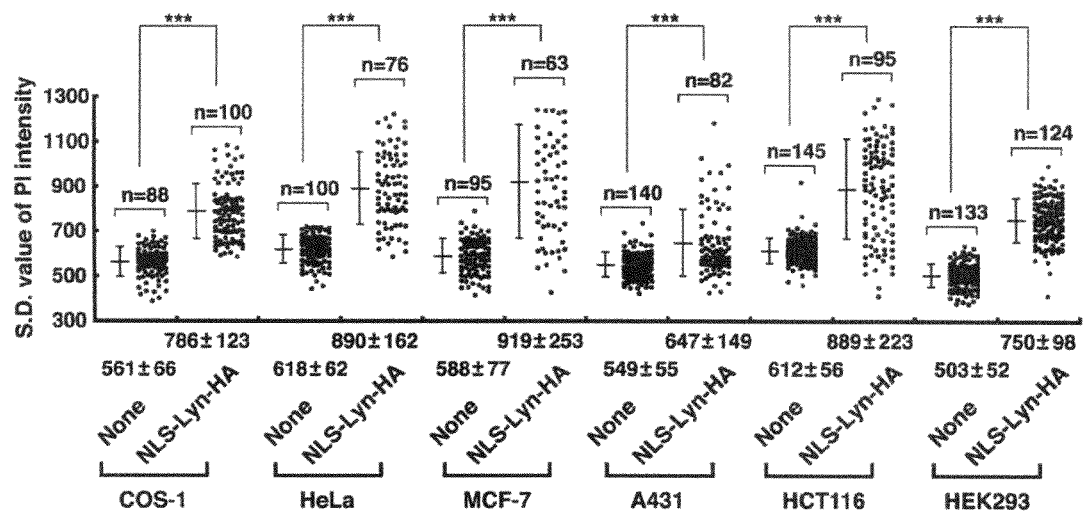
FIG. 44 shows a plot representing each S.D. value of PI intensity per pixel for each cell.
Figure 47A:
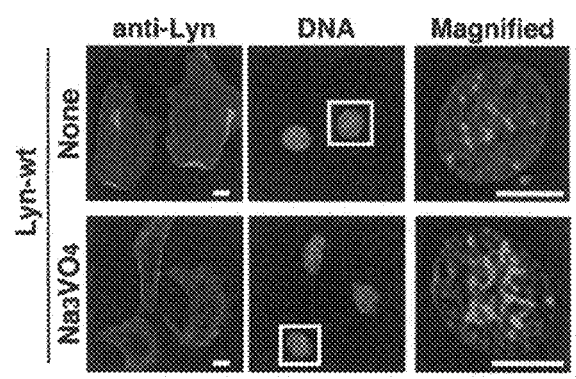
FIG. 47A shows fluorescence imaging of DNA staining for SYF cells stably expressing wild-type Lyn (Lyn-wt) that were treated with nothing or 3 mM $Na_3VO_4$ for 3 h.
Figure 47B:
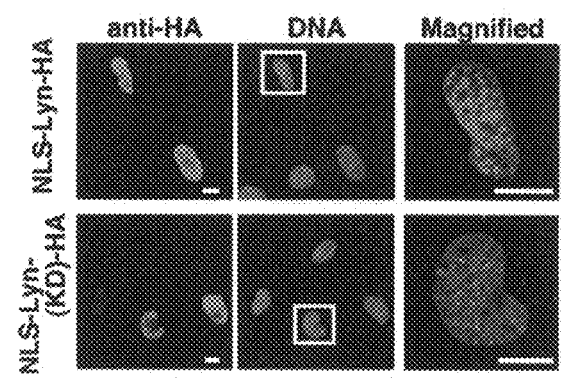
FIG. 47B shows fluorescence imaging of DNA staining for SYF cells that were transfected with NLS-Lyn-HA or NLS-Lyn(KD)-HA and were cultured for 36 h.
Figures 48A, 48B:
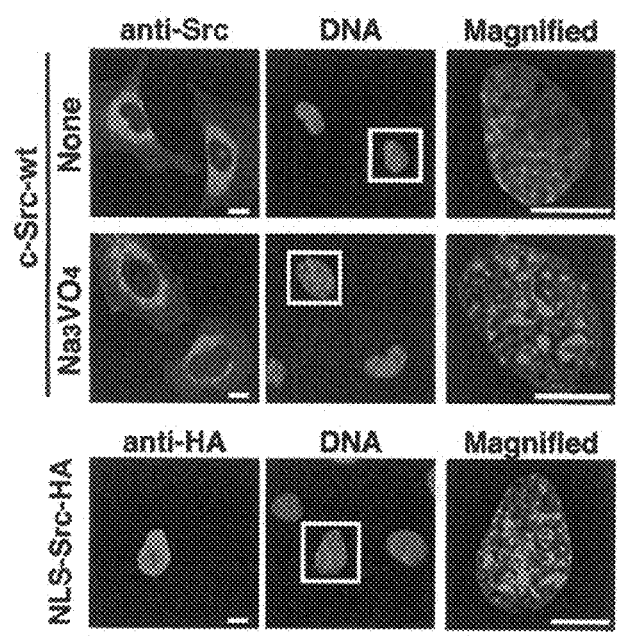
FIG. 48A shows fluorescence imaging of DNA staining for SYF cells stably expressing wild-type c-Src (c-Src-wt) that were treated with nothing or 3 mM $Na_3VO_4$ for 3 h.
FIG. 48B shows fluorescence imaging of DNA staining for SYF cells transfected with NLS-Src-HA that were cultured for 36 h.
Figure 49:
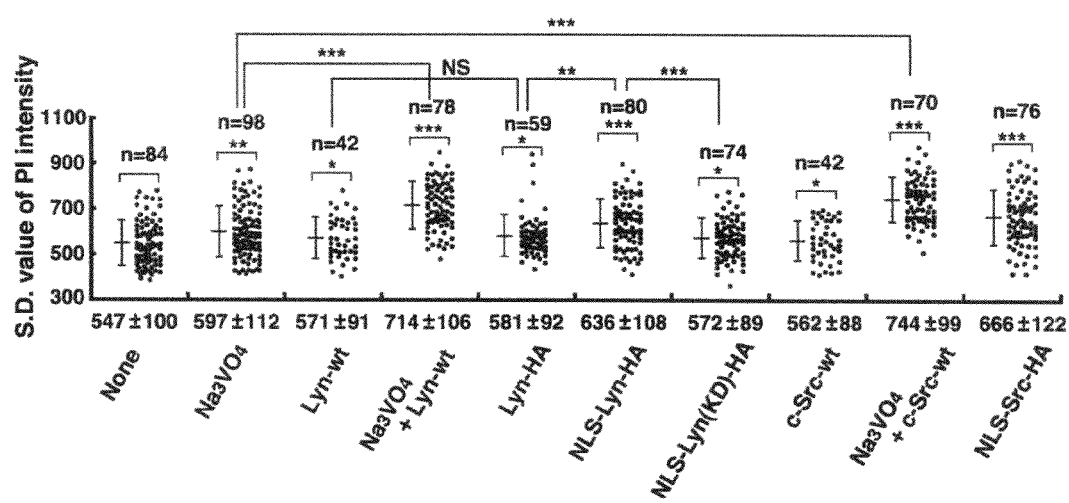
FIG. 49 shows a plot representing each S.D. value of PI intensity per pixel for each cell.
Figures 50A, 50B, 50C:
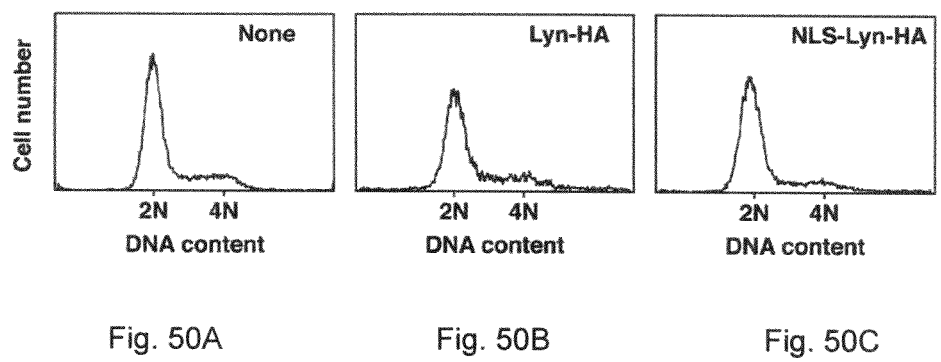
FIGS. 50A-50C show histograms depicting DNA content for SYF cells transfected with nothing, Lyn-HA, and NLS-Lyn-HA, respectively.

FIG. 32 shows schematic representations of NLS-Src-HA, NLS-Lyn-HA, NLS-Lyn(KD)-HA and NLS-Syk. NLS, nuclear localization signal; SH, Src homology domain; PTK, protein-tyrosine kinase domain; HA, HA-epitope tag; KD, kinase-dead K275A mutation. FIGS. 33-34B relate to COS-1 cells transfected with the indicated construct that were cultured for 36 h and doubly stained with anti-pTyr antibody and anti-HA or anti-Syk antibody (FIG. 33), with anti-HA (FIG. 35) or anti-Syk antibody and PI (FIG. 36) or with GFP fluorescence and PI (FIG. 36). Mock indicates transfection with vector alone. Scale bars, 10 μm. Whole cell lysates (FIG. 34A) or nuclear lysates (FIG. 34B) obtained from COS-1 cells transfected with the indicated construct were subjected to Western blotting, probed with anti-pTyr antibody, and sequentially reprobed with anti-HA, anti-Syk, and anti-actin antibodies and with anti-HA and anti-lamin B1 antibodies). FIGS. 35-37 relate to quantitative analysis of localizations of NLS-Src-HA, NLS-Lyn-HA, Lyn-HA, NLS-Lyn(KD)-HA, NLS-Syk, and NLS-GFP. FIG. 37 is a graph showing where protein expression in the nucleus (Nuc) is higher than that in the cytoplasm (Cyto) [Nuc>Cyto]; and where protein expression in the nucleus is lower than or equal to that in the cytoplasm [Nuc≤Cyto]. FIGS. 38A-38C relate to COS-1 cells transfected with nothing, to COS-1 cells transfected with Lyn-HA, or with NLS-Lyn-HA and cultured for 36 h. DNA contents were analyzed by flow cytometry, and results are shown as histograms depicted in FIGS. 38A-38C. The levels of chromatin condensation were assessed using S.D. values of PI intensity per pixel. The plot depicted in FIG. 39 represents each S.D. value of PI intensity per pixel for each cell, and bars and values represent means±S.D. from a representative experiment (51~107 cells) in three independent experiments. Asterisks indicate the significant difference (*p<0.001; NS, not significant) calculated by Student's t-test. FIGS. 40A and 40B relate to COS-1 cells transfected with Flag-Suv39h1 or Flag-G9a were cultured for 36 h and doubly stained with anti-Flag antibody and PI. Scale bars, 10 μm. The levels of chromatin condensation were assessed using S.D. values of PI intensity per pixel, and bars and values represent means±S.D. from a representative experiment (60~109 cells). The plot depicted in FIG. 40B represents each S.D. value of PI intensity per pixel for each cell. Asterisks indicate significant differences (p<0.01; *p<0.001) calculated by Student's t-test. The graphs shown in FIGS. 41 and 42 relate to COS-1 cells transfected with NLS-Lyn-HA or Lyn-HA that were cultured for 24 h and doubly stained with anti-pTyr antibody and PI and with anti-HA antibody and PI. In FIGS. 41 and 42, 2D-plot analyses are shown with S.D. value of PI intensity (vertical axis) versus mean fluorescence intensity of anti-pTyr or anti-HA staining in the nucleus (horizontal axis). n, cell number; r, regression coefficient. FIG. 43 relates to COS-1 cells transfected with NLS-Lyn-HA that were cultured for 24 h and doubly stained with anti-HA antibody and PI, and NLS-Lyn-HA-transfected cells that were also doubly stained with PI and anti-Src[$pY^{418}$], anti-histone H3K4me3, anti-ATF-2 pT69/71, or anti-HP1α antibody, as described under 'Materials and methods'. Scale bars, 10 μm. Various types of cells transfected with or without NLS-Lyn-HA were cultured for 24 h and stained with anti-HA antibody and PI. The levels of chromatin condensation were assessed using S.D. values of PI intensity per pixel, and bars and values represent means±S.D. from a representative experiment (63~145 cells). The plot depicted in FIG. 44 represents each S.D. value of PI intensity per pixel for each cell. Asterisks indicate the significant difference (*p<0.001) calculated by Student's t-test. FIGS. 47A and 47B relate to SYF cells stably expressing wild-type Lyn (Lyn-wt) that were treated with nothing or 3 mM $Na_3VO_4$ for 3 h (FIG. 47A), and SYF cells that were transfected with NLS-Lyn-HA or NLS-Lyn(KD)-HA and were cultured for 36 h (FIG. 47B). Cells were doubly stained with anti-Lyn or anti-HA antibody and PI. Scale bars, 10 μm. FIGS. 48A and 48B relates to SYF cells stably expressing wild-type c-Src (c-Src-wt) that were treated with nothing or 3 mM $Na_3VO_4$ for 3 h (FIG. 48A), and SYF cells transfected with NLS-Src-HA that were cultured for 36 h (FIG. 48B). Cells were doubly stained with anti-Src or anti-HA antibody and PI. Scale bars, 10 μm. FIG. 49 relates to SYF cells were transfected with the indicated construct and treated with $Na_3VO_4$ as described above. The levels of chromatin condensation were assessed using S.D. values of P1 intensity per pixel, and bars and values represent means±S.D. from a representative experiment (42~98 cells) in three independent experiments. The plot represents each S.D. value of PI intensity per pixel for each cell. Asterisks indicate significant differences (*p<0.05; p<0.01; *p<0.001) calculated by Student's t-test. FIGS. 50A-50C relates to SYF cells transfected with nothing, Lyn-HA, or NLS-Lyn-HA that were cultured for 36 h. DNA contents were analyzed by flow cytometry, and results are shown as histograms depicted in FIGS. 50A-50C. FIGS.

Figure 51A:
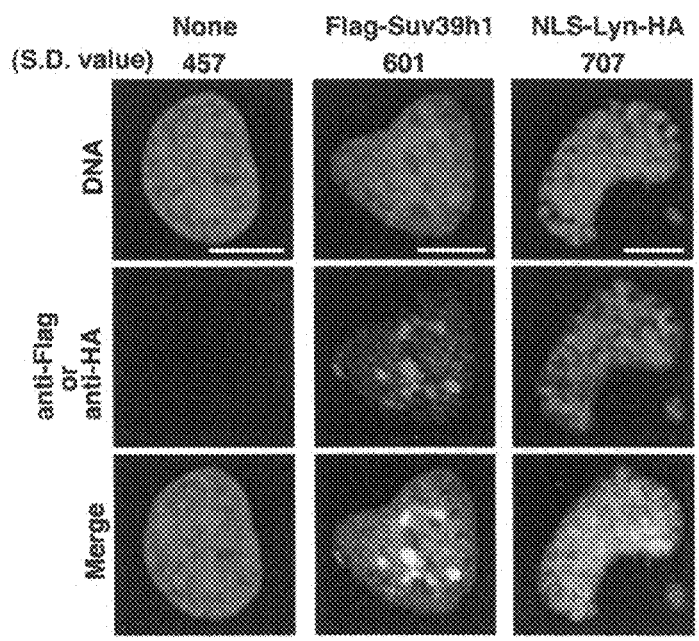
FIG. 51A shows fluorescence imaging of DNA staining for SYF cells transfected with Flag-Suv39h1 and NLS-Lyn-HA that were cultured for 36 h and doubly stained with anti-Flag or anti-HA antibody and PI.
Figure 51B:
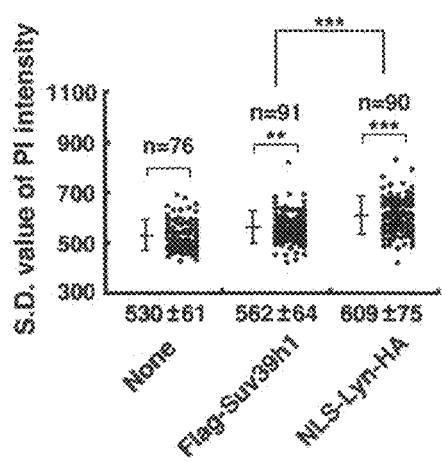
FIG. 51B shows a plot representing each S.D. value of PI intensity per pixel for each cell.
Figure 52:
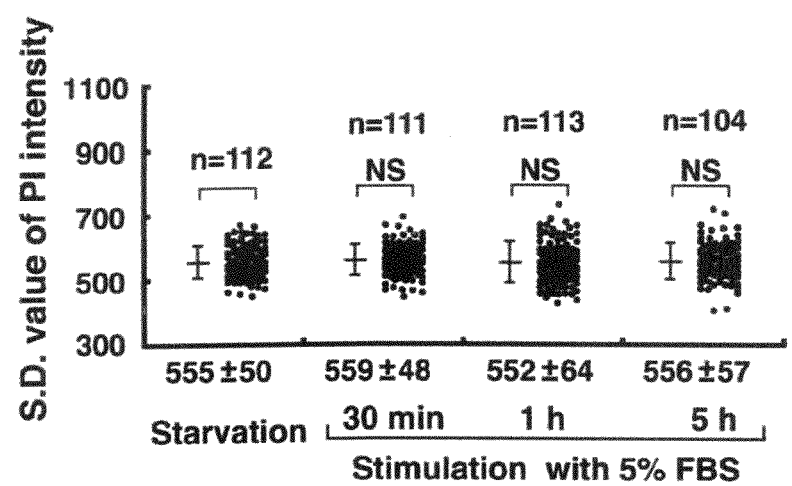
FIG. 52 shows a plot representing each S.D. value of PI intensity per pixel for each cell.
Figure 53:
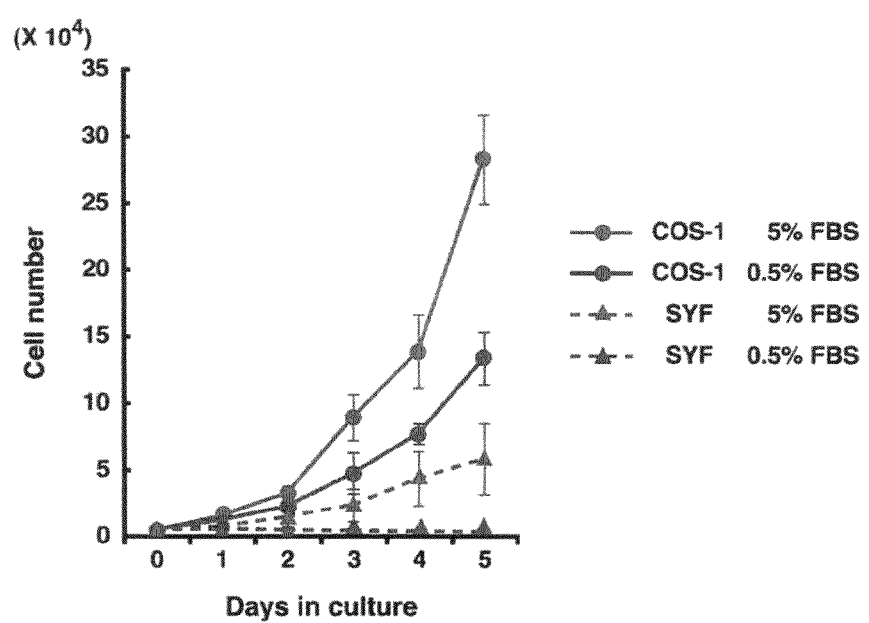
FIG. 53 shows a graph depicting cell numbers that were counted and plotted for COS-1 and SYF cells that were seeded and cultured in 5% FBS for 1 day, and grown in 5% or 0.5% FBS for the indicated periods.

51A and 51B relate to SYF cells transfected with Flag-Suv39h1 and NLS-Lyn-HA that were cultured for 36 h and doubly stained with anti-Flag or anti-HA antibody and PI. In FIG. 51A, the S.D. values of PI intensity are shown on the top. Scale bars, 10 μm. The levels of chromatin condensation were assessed using S.D. values of PI intensity per pixel, and bars and values represent means±S.D. from a representative experiment (76~91 cells). The plot depicted in FIG. 51B represents each S.D. value of PI intensity per pixel for each cell. Asterisks indicate significant differences (p<0.01; *p<0.001) calculated by Student's t-test. FIG. 52 relates to SYF cells that were starved for 24 h under low serum conditions (0.05% FBS), and stimulated with serum (5% FBS) for the indicated times. The plot depicted in FIG. 52 represents each S.D. value of PI intensity per pixel for each cell, and bars and values represent means±S.D. from a representative experiment (104~113 cells). The difference between starvation and stimulation was not significant (NS), as calculated by Student's t-test. FIG. 53 relates to COS-1 and SYF cells that were seeded and cultured in 5% FBS for 1 day, and grown in 5% or 0.5% FBS for the indicated periods. Cell numbers were counted and plotted, as shown, and values represent means±S.D. from triplicate determinations.

A Quantitative Method for Evaluating Chromatin Structural Changes.

Changes in chromatin texture during interphase reflect chromatin structural changes. To define the state of chromatin structure, the quantitative method for evaluating the levels of DNA condensation can be used. For example, the mean and the S.D. value of PI fluorescence intensity per pixel for each cell, as described under 'Materials and methods,' can be computed. FIGS. 1A-1C, 2A-2C, 3A-3C, 4A-4C, 5A-5C, and 6A-6C, show the fluorescence image, histogram, and 2D isometric intensity profile, respectively, corresponding to each computed mean and S.D. value of PI fluorescence intensity. All pixels were classified into three groups as follows: (i) hypocondensed DNA areas (PI intensity per pixel, <2200); (ii) moderately condensed DNA areas (2200≤PI intensity per pixel≤3200); (iii) hypercondensed DNA areas (PI intensity per pixel, >3200). Intriguingly, the histograms and 2D isometric intensity profiles of PI staining revealed that an increase in the S.D. value highly correlated with increased levels of hypo- and hypercondensed DNA, as shown in FIGS. 1A-C and 6A-6C.

In an early study, Feulgen staining of plant cells for DNA showed that condensed chromatin decreased in $G_1$ phase, rapidly increased in S phase, and decreased during $G_2$ phase and the following $G_1$ phase [47]. To test whether the pixel imaging method is sensitive enough to detect cell cycle-dependent changes of DNA condensation, we prepared asynchronized cells, most of which enter $G_1$ phase, and S phase- and $G_2$ phase-enriched cell populations. The histograms of DNA content for the asynchronized cells, S phase-enriched and $G_2$ phase-enriched cell populations are shown in FIGS. 7A, 7B, and 7C, respectively. The histograms of DNA content confirmed enrichment of each cell-cycle phase. Quantitation of DNA condensation utilizing the S.D. value showed a significant, albeit small, increase in the level of DNA condensation during S phase (FIG. 8). To further test whether the pixel imaging method is useful in analyzing DNA condensation during M-phase progression, M phase-enriched cells were prepared and stained with anti-phospho-histone H3S10 antibody and PI for DNA. Given that phosphorylation of histone H3S10 begins during prophase with peak levels detected during metaphase [23], prometaphase was distinguished from prophase by nuclear envelope breakdown and high levels of phospho-histone H3S10. Quantitation of DNA condensation utilizing the S.D. value showed a continuous increase in the level of DNA condensation from prophase to prometaphase during mitotic progression, as shown in the image depicted in FIG. 9, and the corresponding histogram depicted in FIG. 10. Subsequently, to test whether the pixel imaging method can recognize apoptotic DNA condensation, cells were treated with hydrogen peroxide ($H_2O_2$) at 1, 10, and 20 mM. The histograms of DNA content confirmed induction of apoptotic $SubG_1$ cells in a dose-dependent manner, as shown in FIGS. 11A-11D. Quantitation of DNA condensation utilizing the S.D. value, as shown in FIG. 12, showed that the level of DNA condensation corresponded to the degree of apoptosis. These results suggest that the mean of the S.D. value faithfully reflects the level of DNA condensation during the cell cycle and apoptosis induction despite the existence of individual variation. Furthermore, fluorescence images of DNA staining and histone H2B-GFP overlapped completely, as shown in FIG. 13, indicating that the interaction between DNA and histones was retained. Taken together, these results suggest that the levels of chromatin condensation can be quantitated with the S.D. value of PI intensity per pixel. Thus, the pixel imaging, as described herein, can be a useful tool for quantitative analysis of chromatin structural changes.

Growth Factor Stimulation Induces Chromatin Structural Changes.

To examine whether growth factor stimulation altered the state of chromatin condensation, cells were starved for 24 h under low serum conditions for quiescence of growth factor signaling (starvation) and stimulated with serum for 5 h (stimulation). FIGS. 14A and 14B show images of DNA staining with PI for both starvation and stimulation conditions. DNA staining with PI showed that serum stimulation induced a change in chromatin condensation levels. Quantitation of chromatin condensation levels utilizing the S.D. value revealed that serum stimulation rapidly increased both hypo- and hypercondensed chromatin areas, and the increased levels reached a plateau by 30 min, sustained for at least 5 h and returned to the basal levels after 24 h of stimulation, as shown in FIG. 15. Intriguingly, serum-stimulated chromatin hypo- and hypercondensation were significantly inhibited by treatment with PP2, an SFK inhibitor, as shown in FIG. 16. FIGS. 17A and 17B depict histograms of DNA content during the starvation and stimulation. The histograms of DNA content showed no increase in the number of cells in $subG_1$, $G_1$, S, and $G_2$ phases, confirming that the starvation and stimulation treatment does not induce apoptosis or entry into S phase. FIG. 18A shows PI staining for anti-histone H3K4me3 antibody and FIG. 18B shows the corresponding fluorescence intensity plot of anti-histone H3K4me3 antibody. FIG. 19A shows PI staining for anti-ATF-2 pT69/71 antibody and FIG. 19B shows the corresponding fluorescence intensity plot of anti-ATF-2 pT69/71 antibody. FIG. 20A shows PI staining for anti-HP1α antibody and FIG. 20B shows the corresponding fluorescence intensity plot of anti-HP1α antibody. Histone H3 trimethylated on lysine 4 (histone H3K4me3) [48] and transcriptionally active ATF-2 phosphorylated on threonines 69 and 71 (ATF-2 pT69/71) [49, 50] were primarily localized to the areas of hypocondensed chromatin, while heterochromatin protein-1α (HP1α) was largely localized to the areas of hypercondensed chromatin. Importantly, immunostaining with anti-Src[$pY^{418}$] antibody showed that serum stimulation induced activation of SFKs within the nucleus in addition to the cytoplasm. Serum-activated SFKs were more frequently detected in the areas of hypocondensed chromatin than in those of hypercondensed chromatin, as shown in FIG. 21B. These results suggest that growth factor stimulation induces chromatin structural changes through activation of SFKs and increases the areas of both hypocondensed euchromatin and hypercondensed heterochromatin in place of a decrease in the areas of moderately condensed chromatin.

Tyrosine Phosphorylation by SFKs is Involved in Chromatin Structural Changes.

The S.D. value of control cells (None, no treatment) was variable from 450 to 700 (FIGS. 15 and 16), reflecting that the basal level of chromatin condensation fluctuates among individual cells. To test whether SFKs play a role for basal chromatin condensation by regulating the levels of tyrosine phosphorylation, COS-1 cells treated with PP2 or wortmannin, a phosphatidylinositol 3-kinase inhibitor, were doubly stained with anti-phosphotyrosine (pTyr) antibody for tyrosine phosphorylation and PI for DNA. As shown in FIGS. 22 and 26, PP2 treatment was found to significantly reduce the basal levels of tyrosine phosphorylation and chromatin condensation. In contrast, wortmannin treatment did not change the basal levels of chromatin condensation even though it increased the levels of tyrosine phosphorylation, as shown in FIGS. 22 and 26 This increase in tyrosine phosphorylation is reminiscent of the report that wortmannin enhances tyrosine phosphorylation [51]. These results suggest that the basal levels of chromatin condensation involve tyrosine phosphorylation mediated by SFKs.

Figure 54:
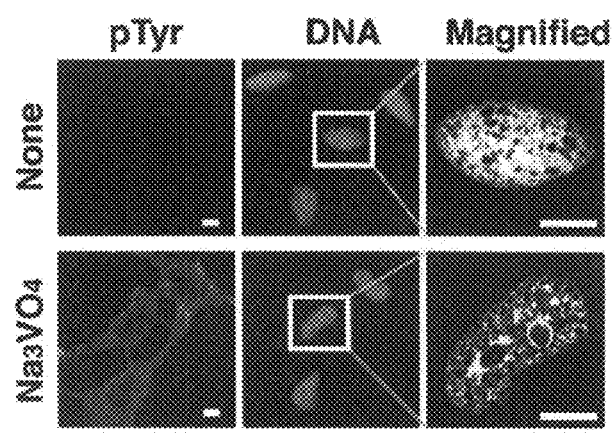
FIG. 54 shows fluorescence images of DNA staining for HeLa cells treated with $Na_3VO_4$ and stained with anti-pTyr antibody and PI.

To clearly visualize tyrosine phosphorylation by immunofluorescent staining, $Na_3VO_4$ (an inhibitor of protein-tyrosine phosphatases; [52]) was used for an increase in tyrosine phosphorylation by inhibiting the activity of tyrosine phosphatases. COS-1 cells treated with $Na_3VO_4$ were stained with anti-pTyr antibody and PI. Treatment with $Na_3VO_4$ greatly increased tyrosine phosphorylation throughout the cell, as shown in FIG. 23, because $Na_3VO_4$ could activate various tyrosine kinases in different subcellular compartments via inhibition of tyrosine dephosphorylation. Intriguingly, treatment with $Na_3VO_4$ induced drastic changes in hypo- and hypercondensed chromatin states, as shown in FIGS. 23 and 26. Similar results were seen in HeLa cells, as shown in FIG. 54. To further examine the contribution of SFK-mediated tyrosine phosphorylation to chromatin structural changes, cells were treated with $Na_3VO_4$ in the presence or absence of PP2. In fact, treatment with PP2 decreased tyrosine phosphorylation, accompanied by a decrease in chromatin hypo- and hypercondensation, as shown in FIGS. 23 and 26.

Since protein-tyrosine phosphatases, including those specific for SFK substrates, are present in the nucleus as well as the cytoplasm [11, 12], it can be assumed that inhibition of tyrosine phosphatases by $Na_3VO_4$ would increase SFK-mediated tyrosine phosphorylation inside the nucleus. To substantiate nuclear phosphorylation, most of cytoplasmic tyrosine-phosphorylated proteins were in situ extracted with 0.5% Triton X-100 at 4° C. for 3 min before fixation. As a result, an increase in tyrosine phosphorylation induced by $Na_3VO_4$ was clearly visible within the nucleus, and an increase in nuclear tyrosine phosphorylation was significantly inhibited by PP2 treatment, as shown in FIGS. 24 and 25. The histograms of DNA content showed no increase in the number of cells in $subG_1$, $G_1$, S, and $G_2$ phases, confirming that treatment with DMSO, PP2, $Na_3VO_4$, or $Na_3VO_4$ plus PP2 does not induce apoptosis or entry into S phase, as shown in FIG. 26. In $Na_3VO_4$-treated cells, tyrosine-phosphorylated proteins as well as histone H3K4me3 and ATF-2 pT69/71 were primarily localized to the areas of hypocondensed chromatin, while HP1α was largely localized to the areas of hypercondensed chromatin, as shown in FIGS. 24 and 28. These results raise the intriguing possibility that nuclear tyrosine phosphorylation by SFKs induces chromatin structural changes.

Nuclear SFKs Mediate Tyrosine Phosphorylation.

Figure 55:
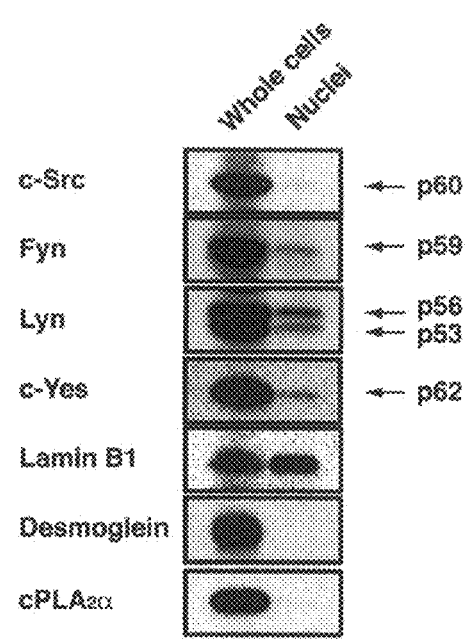
FIG. 55 shows results of Western blotting of highly purified nuclei prepared from HeLa cells.

Previous studies suggest that some of SFKs are present in the nucleus [13, 16, 53]. To further substantiate the nuclear localization of SFKs, highly purified nuclei prepared from COS-1 cells were analyzed by Western blotting. In fact, small fractions of four members of SFKs (c-Src at 60 kDa, c-Yes at 62 kDa, Fyn at 59 kDa, and two alternative splicing isoforms of Lyn at 53 kDa and 56 kDa) were found within purified nuclei, as shown in FIG. 29. Amounts of lamin B1, a nuclear lamina protein, were comparable between the whole cell lysate and the nuclear lysate. Neither the plasma membrane protein desmoglein, nor the Golgi enzyme B-galactosyltransferase (GalT), nor the cytosolic protein cytoplasmic phospholipase $A_2\alpha$ ($cPLA_2\alpha$) was detected in the nuclear lysate, as shown in FIG. 29. Normarski images obviously showed little contamination of other organelle membranes in purified nuclei, as shown in FIG. 30. Similar results were seen in HeLa cells, as shown in FIG. 55. These results indicate that despite their small amounts, SFKs are evidently present in the nucleus.

To test the kinase activity of nuclear SFKs, purified nuclei incubated in vitro with 5 or 10 μM ATP in the presence or absence of 10 μM PP2 were stained with anti-pTyr antibody for tyrosine phosphorylation and PI for DNA. Incubation with ATP increased the levels of nuclear tyrosine phosphorylation, and an increase was significantly inhibited by PP2, as shown in FIGS. 30 and 31. In addition, the amounts of SFKs within purified nuclei were unchanged irrespective of growth factor stimulation (data not shown). These results suggest that SFKs contribute to nuclear tyrosine phosphorylation, implicating that the kinase activity of nuclear SFKs plays a role in the nuclear architecture.

Introduction of SFKs into the Nucleus Causes Chromatin Structural Changes.

Figure 56A:
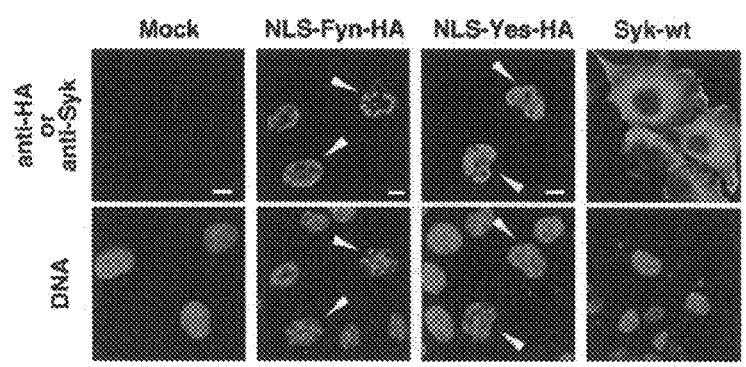
FIG. 56A shows fluorescence imaging of DNA staining for COS-1 cells transfected with NLS-Yes-HA (kinase-active) and NLS-Fyn-HA (kinase-active).
Figure 56B:
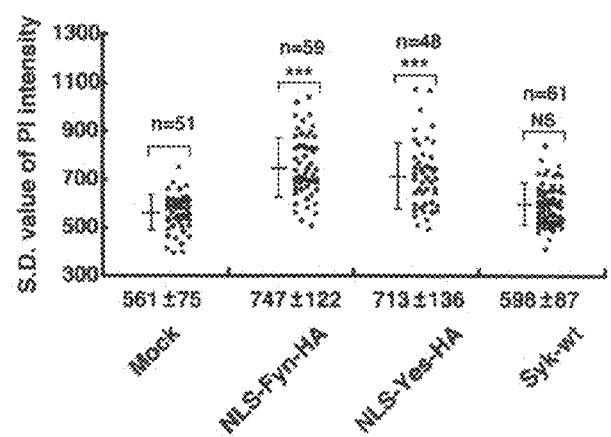
FIG. 56B shows a plot representing each S.D. value of PI intensity per pixel for each cell.

To substantiate the involvement of nuclear SFKs in chromatin condensation, several mutants were constructed that were tagged with a nuclear localization signal (NLS), as shown in FIG. 32, and transfected COS-1 cells with these constructs. NLS-Src-HA (kinase-active), NLS-Lyn-HA (kinase-active), NLS-Lyn(KD)-HA (kinase-dead), and NLS-Syk (unrelated kinase) were all accumulated in the nucleus, as shown FIGS. 33 and 35. Immunofluorescent staining with anti-pTyr antibody showed that the increased levels of tyrosine phosphorylation in the nucleus were comparable among cells expressing NLS-Src-HA, NLS-Lyn-HA, and NLS-Syk, as shown in FIG. 33, and Western blotting with anti-pTyr antibody confirmed the appearance of tyrosine-phosphorylated proteins in purified nuclei prepared from cells transfected with NLS-Src-HA or NLS-Lyn-HA, as shown in FIGS. 34A and 34B. It is of interest to note that despite only a small increase in cell populations in S phase, chromatin hypo- and hypercondensation were strikingly induced by NLS-Src-HA and NLS-Lyn-HA even in the absence of $Na_3VO_4$ as shown in FIGS. 35 and 36, arrowheads and FIGS. 38A-38C and 39. The other SFK members, NLS-Yes-HA (kinase-active) and NLS-Fyn-HA (kinase-active), similarly induced chromatin hypo- and hypercondensation, as shown in FIGS. 56A and 56B. However, NLS-Syk, shown in FIGS. 35, 36, and 39, and Syk-wt, shown in FIGS. 56A and 56B, did not significantly induce chromatin hypo- and hypercondensation, presumably because low sequence similarity of Syk to SFKs in the catalytic region (only 40 to 45%) causes the different substrate specificity [54]. As nuclear accumulation of an irrelevant protein, such as NLS-GFP, may somehow bring about chromatin hypo- and hypercondensation, NLS-Lyn(KD)-HA, despite having very weak kinase activity, shown in FIGS. 34A and 34B, would be a good control of NLS-Lyn-HA. Furthermore, we performed additional control experiments with the histone H3K9 methyltransferases Flag-Suv39h1 and Flag-G9a, which participate in heterochromatin formation [32] and transcriptional repression in euchromatic areas [55]. Chromatin condensation was modestly induced by Flag-Suv39h1 and Flag-G9a, as shown in FIGS. 40A and 40B. Note that the levels of chromatin condensation were much lower than those by NLS-Lyn-HA (compare FIGS. 40A and 40B with FIG. 39).

Figure 61:
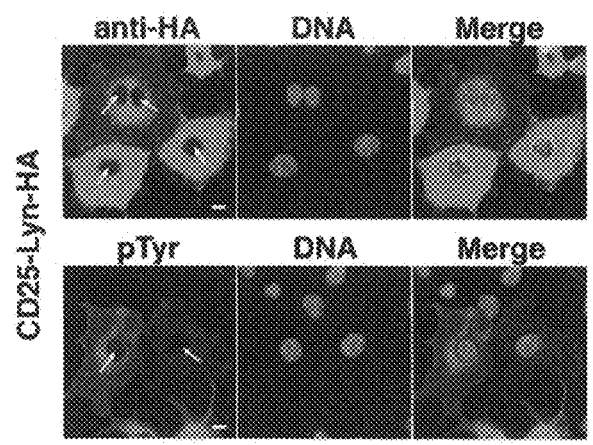
FIG. 61 shows fluorescence images of DNA staining for COS-1 cells transfected with CD25-Lyn-HA were cultured for 24 h and doubly stained with anti-HA or anti-pTyr antibody and PI.
Figure 62:
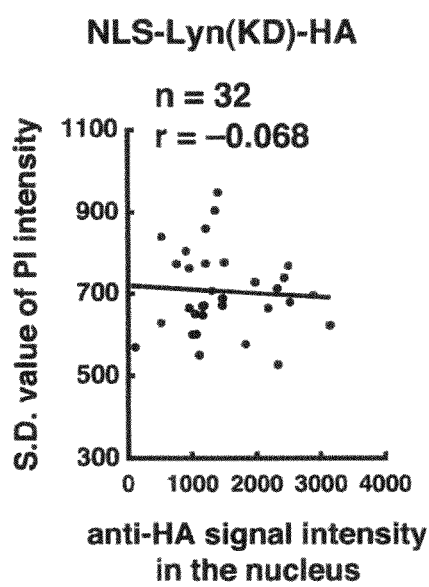
FIG. 62 shows 2D-plot analyses shown with S.D. value of PI intensity (vertical axis) versus mean fluorescence intensity of anti-HA staining in the nucleus (horizontal axis) in NLS-Lyn(KD)-HA-transfected cells.
Figure 63:
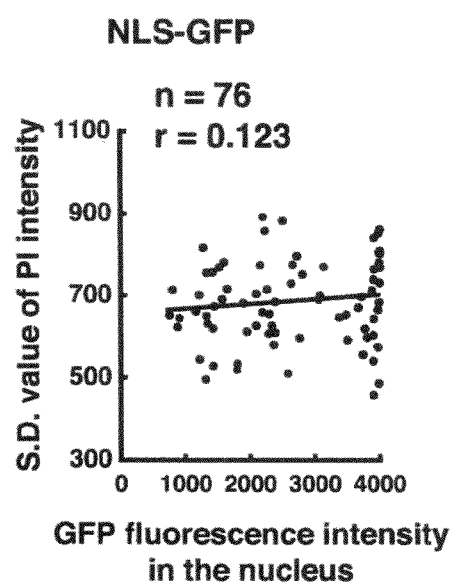
FIG. 63 shows 2D-plot analyses shown with S.D. value of PI intensity (vertical axis) versus mean fluorescence intensity of GFP in the nucleus (horizontal axis) in NLS-GFP-transfected cells.

To examine the correlation between the intensity of nuclear tyrosine phosphorylation and the S.D. value of PI intensity in individual nuclei, 2D-plot analysis was performed on COS-1 cells transfected with NLS-Lyn-HA. FIG. 41 shows that the levels of nuclear pTyr signals positively correlated with S.D. values, suggesting that higher levels of nuclear tyrosine phosphorylation lead to more intense hypo- and hypercondensation of chromatin. On the other hand, kinase-active Lyn-HA, only a fraction of which was localized in the nucleus, as shown in FIG. 37, induced lower levels of chromatin hypo- and hypercondensation than NLS-Lyn-HA, as shown in FIG. 39. 2D-plot analyses of the correlation of the S.D. value of PI intensity was performed with the levels of nuclear accumulation of Lyn-HA and with those of nuclear pTyr signals relative to whole cell pTyr signals on COS-1 cells transfected with Lyn-HA, and found that the S.D. values positively correlated with both the protein levels of nuclear Lyn-HA and the levels of nuclear tyrosine phosphorylation, as shown in FIGS. 42 and 57. To attempt to construct a Lyn mutant that is not imported into the nucleus, a CD25-Lyn-HA chimera was generated containing a transmembrane domain and a signal sequence for secretory proteins. CD25-Lyn-HA was an approximately 92-kDa doublet and mainly localized to the plasma membrane, but a fraction of CD25-Lyn-HA was in fact detected within the nucleus (FIG. 61 arrows). However, like Lyn-HA, 2D-plot analysis showed a correlation between the levels of nuclear tyrosine phosphorylation and the S.D. values in COS-1 cells expressing CD25-Lyn-HA, as shown in FIG. 59A. In other words, high expression of CD25-Lyn-HA in the cytoplasm was not able to account for the induction of chromatin hypo- and hypercondensation. In addition, given that a fraction of the receptor-type tyrosine kinase ErbB3 localizes in the nucleus without cleavage [56], it may be difficult to circumvent nuclear import of CD25-Lyn-HA. Furthermore, 2D-plot analysis showed that there was no correlation between the protein levels of NLS-Lyn(KD)-HA and of NLS-GFP and the S.D. values, as shown in FIGS. 62, 63, and FIG. 39).

NLS-Lyn-HA as well as histone H3K4me3 and ATF-2 pT69/71 were primarily localized in the areas of hypocondensed chromatin, while HP1α was largely localized to the areas of hypercondensed chromatin, as shown in FIGS. 43, 19A, 19B, and 28. Importantly, immunostaining with anti-Src[pY$^{418}$] antibody showed that activated NLS-Lyn-HA were largely localized in the areas of hypocondensed chromatin, as shown in FIG. 43 and FIGS. 21A and 21B. Furthermore, the results of SFK-mediated chromatin structural changes, similar to those from monkey fibroblast COS-1 cells, were obtained from human epithelial HeLa cells, human breast MCF-7 cells, human epithelial A431 cells, human colon HCT116 cells and human embryonic kidney HEK293 cells, as shown in FIG. 44. These results suggest that nuclear tyrosine phosphorylation mediated by SFKs is responsible for chromatin structural changes.

Figure 45A:
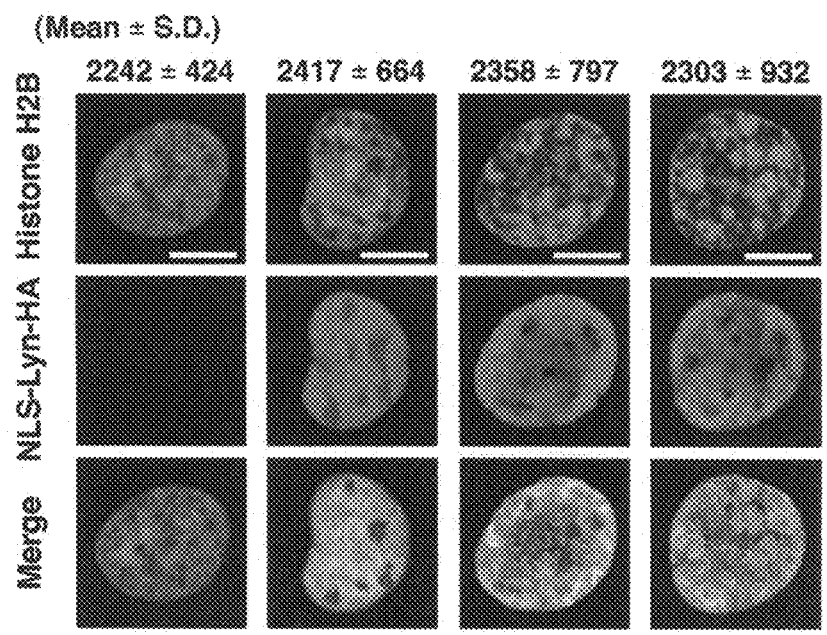
FIG. 45A shows fluorescence images of DNA staining for COS-1 cells stably expressing histone H2B-GFP that were transfected with NLS-Lyn-HA.
Figure 45B:
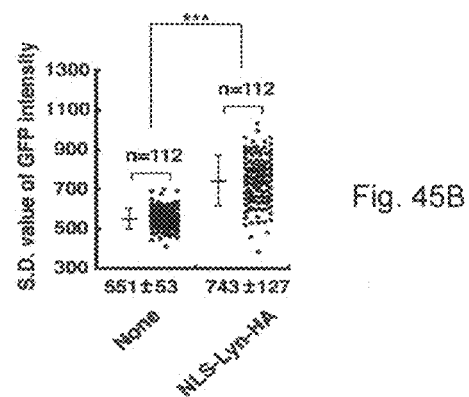
FIG. 45B shows a plot representing each S.D. value of PI intensity per pixel for each cell.

In addition, because of the complete overlap of fluorescence images between DNA staining and histone H2B-GFP, as shown in FIG. 13, further investigation was conducted to determine whether the levels of chromatin hypo- and hypercondensation were quantitated using the S.D. value of GFP fluorescence intensity per pixel for each nucleus. Similar to the S.D. value of PI fluorescence, NLS-Lyn-HA greatly increased the levels of GFP fluorescence intensity, as shown in FIG. 45B, indicating that chromatin hypo- and hypercondensation can be quantitated using the S.D. values of histone H2B-GFP fluorescence as well as those of PI fluorescence.
SFKs are Required for Chromatin Structural Changes.

Figure 46:
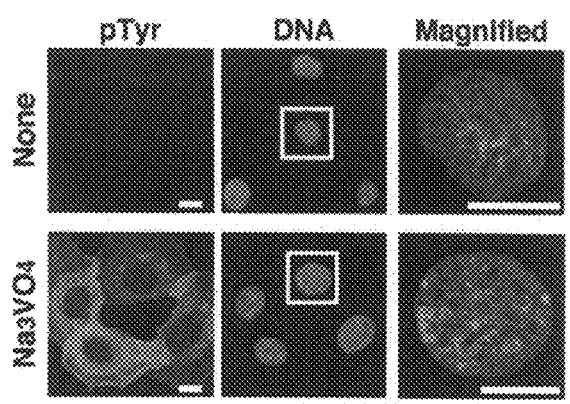
FIG. 46 shows fluorescence imaging of DNA staining for SYF cells treated with nothing or with 3 mM $Na_3VO_4$ for 3 h and doubly stained with anti-pTyr antibody and PI.

To examine the requirement of endogenous SFKs for chromatin condensation, mouse embryonic fibroblast SYF cells were used, which are genetically deficient in expression of c-Src, c-Yes and Fyn and do not express Lyn at a detectable level [37]. Although treatment of SYF cells with Na$_3$VO$_4$ increased tyrosine phosphorylation at levels comparable to those in COS-1 cells (compare FIG. 46 with FIG. 23), the levels of chromatin hypo- and hypercondensation in Na$_3$VO$_4$-treated SYF cells were much lower than those in Na$_3$VO$_4$-treated COS-1 cells (compare FIG. 49 with FIG. 26). These results suggest that tyrosine phosphorylation primarily mediated by SFKs contributes to chromatin structural changes.

Next, the add-back version of SYF cells expressing wild-type Lyn (SYF/Lyn-wt cells) or wild-type c-Src (SYF/c-Src-wt cells) was established. SYF/Lyn-wt cells, in which nuclear localization of a small fraction of Lyn was detected by anti-Lyn immunofluorescence, as shown in FIGS. 47A and 47B, showed a slight increase in the levels of chromatin hypo- and hypercondensation, and treatment of SYF/Lyn-wt cells with Na$_3$VO$_4$ was able to increase chromatin hypo- and hypercondensation, as shown in FIGS. 47A, 47B, and 49. In addition, transfection of kinase-active Lyn-HA into SYF cells induced only a slight increase in the levels of chromatin hypo- and hypercondensation, probably due to its slight expression in the nucleus. Without Na$_3$VO$_4$ treatment, SYF cells transfected with kinase-active NLS-Lyn-HA, but not kinase-inactive NLS-Lyn(KD)-HA, exhibited increased levels of chromatin hypo- and hypercondensation, as shown in FIGS. 47A, 47B, and 49, although the levels were modest in SYF cells compared with those in COS-1 cells (compare FIG. 49 with FIG. 39). Likewise, an increase in chromatin hypo- and hypercondensation was seen in SYF/c-Src-wt cells treated with Na$_3$VO$_4$ and in SYF cells transfected with NLS-Src-HA (FIGS. 48A and 49). The histograms of DNA content showed that expression of Lyn-HA or NLS-Lyn-HA did not affect the cell cycle of SYF cells (FIGS. 50A-50C). Flag-Suv39h1 largely localized to heterochromatic areas, but only modestly induced chromatin condensation (FIGS. 51A and 51B see FIG. 52). The levels of chromatin condensation induced by Flag-Suv39h1 were lower than those by NLS-Lyn-HA, which predominantly localized to euchromatic areas. These results suggest that SFK-mediated tyrosine phosphorylation within the nucleus may contribute to chromatin hypo- and hypercondensation through euchromatinization and concomitant heterochromatinization.

Furthermore, to test whether stimulation of SYF cells with serum growth factors induced chromatin hypo- and hypercondensation, SYF cells were starved for 24 h under low serum conditions (starvation) and stimulated with 5% FBS for 30 min, 1 h, and 5 h (stimulation). FIG. 52 shows that serum stimulation did not induce any chromatin structural changes in SYF cells. Cell proliferation between SYF and COS-1 cells was compared, both of which express SV40 large T antigen. Intriguingly, SYF cells exhibited much slower rates of cell proliferation than COS-1 cells, since SYF cells poorly responded to serum growth factors for cell proliferation, as shown in FIG. 53. Taken together with the finding that COS-1 cells co-express four members of SFKs, i.e. c-Src, c-Yes, Fyn and Lyn, as shown in FIG. 29 ([57]), these results suggest that cell proliferation is seriously affected by the lack of expression of SFK members.

Dynamic nuclear structural changes are frequently observed during transcription, terminal cell differentiation, senescence, tumorigenesis, and cell cycle [21, 58, 59]. The quantitative method for determining the levels of chromatin condensation and demonstrate, as described herein, was used to demonstrate that nuclear tyrosine phosphorylation by SFKs is required for growth factor-stimulated induction of euchromatic hypocondensation and concomitant heterochromatic hypercondensation. Based on the findings described herein, it can be concluded that an association of SFKs with euchromatinization and heterochromatinization upon growth factor stimulation does exist.

The pixel imaging method allows levels of chromatin condensation to be quantitated during the cell cycle, including mitotic progression, and also during apoptosis induction (FIGS. 1A-1C and FIGS. 6A-6C). Using this method, changes in chromatin condensation upon growth factor stimulation (FIGS. 15 and 16) can be detected, suggesting a correlation between the alteration of chromatin condensation and the cell cycle transition from $G_0$ to $G_1$ phase. Intriguingly, growth factor-induced chromatin structural changes are largely mediated by the tyrosine kinase-activity of SFKs (FIGS. 14A, 14B, and FIG. 52). Inside the nucleus, kinase-active SFKs localize predominantly to euchromatic hypocondensed areas, whereas a small fraction of kinase-active SFKs is localized to heterochromatic hypercondensed areas (FIGS. 21A, 21B, and FIG. 43). However, changes in chromatin structure have little influence on the expression levels of histone H3K4me3 and ATF-2 pT69/71 (data not shown), suggesting that chromatin structural changes mediated by SFKs do not seem to directly increase transcription activity. Rather, kinase-active SFKs in the nucleus may be primarily involved in formation of "open chromatin", which enables transcription factors to access to genes, and concomitant development of "closed chromatin". Conversely, Suv39h1 is involved in heterochromatin formation and predominantly localizes to heterochromatic areas [32], and overexpression of Suv39h1 induces modest chromatin condensation (FIGS. 40A, 40B, 51A, and 51B). Since the levels of chromatin condensation by Suv39h1 were lower than those by nuclear SFKs (FIGS. 40A and 39), nuclear tyrosine phosphorylation by SFKs plays a dynamic role in chromatin architecture. Assumingly, growth factor stimulation would transmit signals to the induction of not only chromatin hypocondensation but also hypercondensation through SFK-mediated tyrosine phosphorylation.

Transfection of COS-1 cells with kinase-active NLS-SFKs induces strong chromatin condensation, i.e. induction of both euchromatinization and heterochromatinization, and higher levels of nuclear tyrosine phosphorylation lead to more intense hypo- and hypercondensation of chromatin (FIGS. 41 and 58). Although transfection of COS-1 cells with kinase-active Lyn-HA, which in part localizes in the nucleus, induces weak chromatin condensation (FIG. 39), both the protein levels of Lyn-HA in the nucleus and the levels of nuclear tyrosine phosphorylation positively correlate with the levels of chromatin hypo- and hypercondensation (FIGS. 42 and 57). In case of NLS-GFP and NLS-Lyn(KD)-HA but not NLS-Syk, nuclear expression of proteins may somehow give rise to chromatin condensation (FIG. 39; see also FIGS. 62 and 63). Nonetheless, the effect of NLS-Lyn-HA on chromatin condensation is significantly stronger than that of NLS-Lyn(KD)-HA, as shown in FIG. 39. Thus, the results suggest that nuclear tyrosine phosphorylation by SFKs plays a critical role in chromatin hypo- and hypercondensation.

SFK members form the largest subfamily among nonreceptor-type tyrosine kinases [60], and four SFK members, c-Src, Fyn, Lyn and c-Yes, are widely co-expressed in epithelial and fibroblastic cells (FIGS. 29 and 55; [57]). Multiple combinations in expression of each SFK member in a single cell can serve specific and overlapping functions for signal transduction through tyrosine phosphorylation. Given that SYF cells, which do not express detectable Lyn and lack c-Src, c-Yes and Fyn, are incapable of inducing chromatin hypo- and hypercondensation upon serum growth factor stimulation (FIG. 52), a poor proliferative response of SYF cells to serum growth factors (FIG. 53) may be related to the inability to induce chromatin hypo- and hypercondensation.

The basal levels of chromatin condensation indeed fluctuate in individual SYF cells and PP2-treated COS-1 cells (FIGS. 15-16, 26, 39, 40A, 49, 51A, and 52), and chromatin structural changes are modestly induced in $Na_3VO_4$-treated SYF cells (FIG. 49). These results suggest that alternative pathways, if any, might involve some tyrosine kinases other than SFKs. Treatment of cells with U0126, an inhibitor of MEK1/2, slightly decreased the basal levels of chromatin condensation (data not shown), implicating limited involvement of the MEK/ERK pathway in chromatin condensation. Recent studies showed that dynamic changes in chromatin structure are induced by heat shock, osmotic stress, and ATP depletion [61-63], although the appearance does not seem to be identical. Hyperosmolar conditions had no effect on tyrosine phosphorylation and treatment with PP2 did not inhibit hyperosmotic stress-induced chromatin structural changes (data not shown). These results suggest that chromatin structure changes may involve a wide variety of stimulation. Nonetheless, it should be emphasized that upon growth factor stimulation, SFKs play an important role in chromatin structural changes through tyrosine phosphorylation within the nucleus.

Human DNA encodes 518 protein kinases, with 428 known or predicted to phosphorylate serine and threonine residues and 90 belonging to the tyrosine kinase family [64]. The nucleus contains a large number of proteins phosphorylated on serine and/or threonine residues. Serine/threonine phosphorylation of histones is involved in mitotic chromosome condensation, apoptosis, gametogenesis, and gene expression [22, 23, 65-67], and a cycle of serine/threonine phosphorylation and dephosphorylation is involved in the recruitment of splicing factors from splicing speckles to site of transcription [68]. Many serine/threonine kinases in budding yeast physically occupy their target genes and affect gene expression [69]. On the other hand, there is a limited number of studies that show the nuclear localization and function of tyrosine kinases and phosphatases. For instance, c-Abl tyrosine kinase present in the nucleus plays a role in cell proliferation, DNA damage and stress response, and nuclear PEP-PTP tyrosine phosphatase is implicated in dephosphorylation of SFKs and their substrates [10-12]. Recent studies showed that the cyclin-dependent kinase inhibitor p27 is identified as a nuclear substrate of SFKs [18, 19]. However, at present nothing is known about nuclear substrates of SFKs in SFK-mediated chromatin structural changes.

SFKs are activated in differentiation, tumorigenesis, cell cycle and transcription [2, 70]. Previously, chromatin structural changes, including a change from a finely textured to a coarse heterochromatic appearance, were observed in cell lines expressing oncogenic v-Src as well as H-Ras [71]. Specific tumor types are associated with characteristic alterations of chromatin texture, such as coarse aggregates of heterochromatin, asymmetric aggregates of heterochromatin, dispersed heterochromatin and loss of heterochromatin aggregates [21]. Changes in heterochromatin content and chromatin texture and shape are closely associated with more aggressive breast tumors [72]. The pixel imaging method can be helpful in quantitatively analyzing the alterations of chromatin texture in various cancer types and clinical stages.

On the basis of the results, the significance of SFK-mediated nuclear tyrosine phosphorylation in chromatin structural changes is evident.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for diagnosis of a lesion in a subject comprising evaluating the chromatin structure in a sample of one or more lesion cells from the subject in vitro, said evaluating comprising:
   providing a sample of one or more cells from the lesion in vitro;
   treating the one or more cells with a nucleic acid stain;
   capturing an image of a nucleus of one or more of the nucleic acid stain treated cells, the image comprising a plurality of pixels;
   quantitating the stain intensity at each pixel of the plurality of pixels;
   calculating the mean and standard deviation (SD) values of stain intensity per pixel;
   determining the chromatin structure wherein the SD value is indicative of the level of chromatin condensation, the level of chromatin condensation is indicative of a disease state, an increase in chromatin condensation and an increase of the SD value are indicative of progression toward the disease state, and the disease state is breast cancer or a cancer expressing c-Src, v-Src, or H-Ras; and
   evaluating the chromatin structure in a sample of one or more non-lesion cells from the subject and comparing the calculated SD value of the one or more lesion cells with the calculated SD value of the one or more non-lesion cells to determine whether or not there is an increase of chromatin condensation and an increase of the SD value in the one or more lesion cells.

2. The method of claim 1, wherein the providing, treating, capturing, quantitating, calculating, and determining are repeated after a predetermined time has elapsed to determine whether the lesion has progressed toward or regressed away from the disease state.

3. The method of claim 2, wherein the progression of the lesion during the predetermined time is utilized to measure the efficacy of a method for treating the lesion.

4. The method of claim 1, wherein the cancer is a cancer expressing c-Src, v-Src, or H-Ras.

5. The method of claim 1, wherein the cancer is breast cancer.

6. A method for diagnosis of a lesion in a subject comprising evaluating the chromatin structure in a sample of one or more lesion cells from the subject in vitro, said evaluating comprising:
   providing a sample of one or more cells from the lesion in vitro;
   treating the one or more cells with a nucleic acid stain;
   capturing an image of a nucleus of one or more of the nucleic acid stain treated cells, the image comprising a plurality of pixels;
   quantitating the stain intensity at each pixel of the plurality of pixels;
   calculating the mean and standard deviation (SD) values of stain intensity per pixel;

determining the chromatin structure wherein the SD value is indicative of the level of chromatin condensation, the level of chromatin condensation is indicative of a disease state, an increase in chromatin condensation and an increase of the SD value are indicative of progression toward the disease state, and the disease state is breast cancer or a cancer expressing c-Src, v-Src, or H-Ras; and comparing the calculated SD value of the one or more lesion cells to a range of previously calculated SD values of the same type of lesion located along a progression curve from normal tissue to the disease state to determine whether or not there is an increase of the SD value and an increase of chromatin condensation in the one or more lesion cells.

7. The method of claim 6, wherein the cancer is a cancer expressing c-Src, v-Src, or H-Ras.

8. The method of claim 6, wherein the cancer is breast cancer.

* * * * *